(12) United States Patent
Kassab

(10) Patent No.: US 8,979,786 B2
(45) Date of Patent: Mar. 17, 2015

(54) AUTORETROPERFUSION DEVICES AND SYSTEMS

(75) Inventor: Ghassan S. Kassab, Zionsville, IN (US)

(73) Assignee: CVDevices, LLC, San Diego, CA (US)

( * ) Notice: Subject to any disclaimer, the term of this patent is extended or adjusted under 35 U.S.C. 154(b) by 46 days.

(21) Appl. No.: 13/125,512

(22) PCT Filed: Dec. 19, 2008

(86) PCT No.: PCT/US2008/087863
§ 371 (c)(1),
(2), (4) Date: Apr. 21, 2011

(87) PCT Pub. No.: WO2010/071659
PCT Pub. Date: Jun. 24, 2010

(65) Prior Publication Data
US 2011/0208109 A1   Aug. 25, 2011

(51) Int. Cl.
*A61M 37/00* (2006.01)
*A61M 5/00* (2006.01)
*A61M 25/00* (2006.01)
(Continued)

(52) U.S. Cl.
CPC ........ *A61M 25/0021* (2013.01); *A61B 5/02152* (2013.01); *A61B 5/02158* (2013.01); *A61B 5/026* (2013.01); *A61B 5/6853* (2013.01); *A61M 25/04* (2013.01); *A61M 25/10* (2013.01); *A61M 25/104* (2013.01); *A61M 2025/1052* (2013.01);
(Continued)

(58) Field of Classification Search
CPC . A61M 25/0021; A61M 25/04; A61M 25/10; A61M 25/104; A61M 2205/1052; A61M 2205/3334; A61M 2205/3523; A61M 2205/3561; A61B 5/02152; A61B 5/02158; A61B 5/026; A61B 5/6853
USPC .................. 604/8, 9, 4.01–6.16; 623/1.35
See application file for complete search history.

(56) References Cited

U.S. PATENT DOCUMENTS 4,318,401 A   3/1982   Zimmerman
4,957,110 A   9/1990   Vogel et al.
(Continued)

FOREIGN PATENT DOCUMENTS

JP   U-H06-021648   3/1994
WO   WO 2008/144382   11/2008

OTHER PUBLICATIONS

PCT/US2008/087863, PCT Search Report dated Feb. 13, 2009.
(Continued)

*Primary Examiner* — Philip R Wiest
*Assistant Examiner* — Benjamin Klein
(74) *Attorney, Agent, or Firm* — Reichel IP LLP; Mark C. Reichel; Natalie J. Dean

(57) ABSTRACT

Devices, systems, and methods for providing retroperfusion to at least one ischemic tissue in a minimally invasive manner are disclosed. At least some of the embodiments disclosed herein enable an anastomosis to be formed between a vein and an artery without the use of sutures and through a non-invasive procedure. In addition, various disclosed embodiments provide a cannula device comprising a Y-configuration for bifurcating arterial flow between an anastomosis and the underlying artery. The devices, systems and methods herein can further provide simultaneous autoretroperfusion therapy to more than one area of an ischemic tissue.

21 Claims, 16 Drawing Sheets

(51) Int. Cl.
　　　*A61B 5/0215*　　(2006.01)
　　　*A61B 5/026*　　(2006.01)
　　　*A61B 5/00*　　(2006.01)
　　　*A61M 25/04*　　(2006.01)
　　　*A61M 25/10*　　(2013.01)

(52) U.S. Cl.
　　　CPC .............. *A61M 2205/3334* (2013.01); *A61M 2205/3523* (2013.01); *A61M 2205/3561* (2013.01)
　　　USPC ............................................. 604/4.01; 604/8

(56) References Cited

U.S. PATENT DOCUMENTS

| | | | |
|---|---|---|---|
| 5,273,534 A | 12/1993 | Knoepfler | |
| 5,511,553 A | 4/1996 | Segalowitz | |
| 5,655,548 A | 8/1997 | Nelson et al. | |
| 6,053,901 A | 4/2000 | Finch, Jr. et al. | |
| 6,186,972 B1 | 2/2001 | Nelson et al. | |
| 6,241,699 B1 * | 6/2001 | Suresh et al. | 604/7 |
| 7,004,925 B2 | 2/2006 | Navia et al. | |
| 7,004,926 B2 | 2/2006 | Navia et al. | |
| 7,112,211 B2 * | 9/2006 | Gifford et al. | 606/153 |
| 7,473,237 B2 * | 1/2009 | Navia et al. | 604/6.13 |
| 7,819,856 B2 | 10/2010 | Bates | |
| 2003/0125798 A1 | 7/2003 | Martin | |
| 2003/0181843 A1 | 9/2003 | Bibber et al. | |
| 2006/0184088 A1 | 8/2006 | Van Bibber et al. | |
| 2006/0224232 A1 * | 10/2006 | Chobotov | 623/1.16 |
| 2007/0010781 A1 | 1/2007 | Vijay | |
| 2008/0234658 A1 | 9/2008 | Kassab et al. | |

OTHER PUBLICATIONS

PCT/US2008/087863, PCT Written Opinion dated Feb. 13, 2009.

* cited by examiner

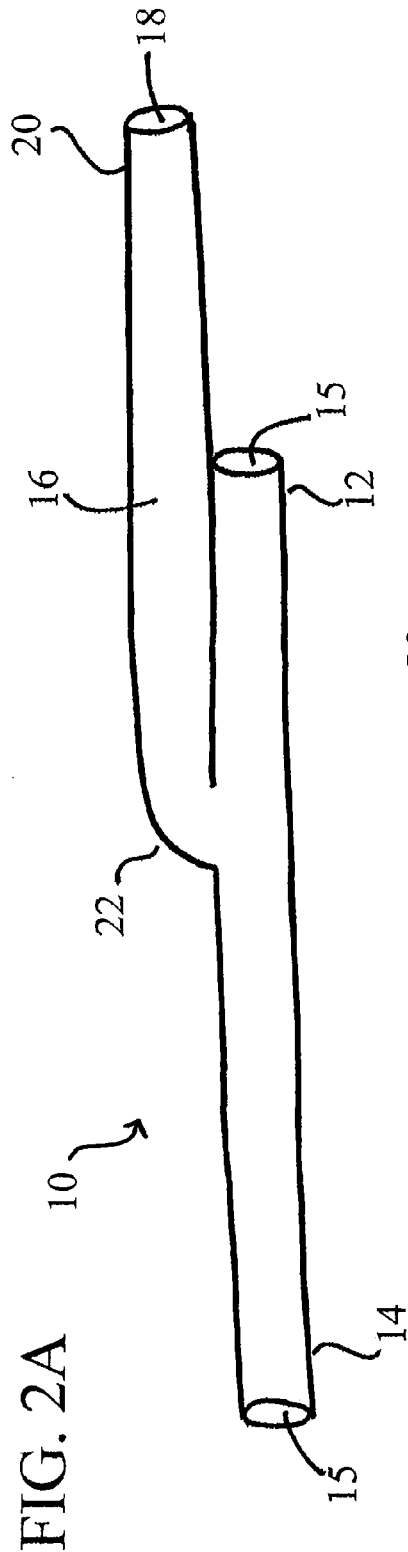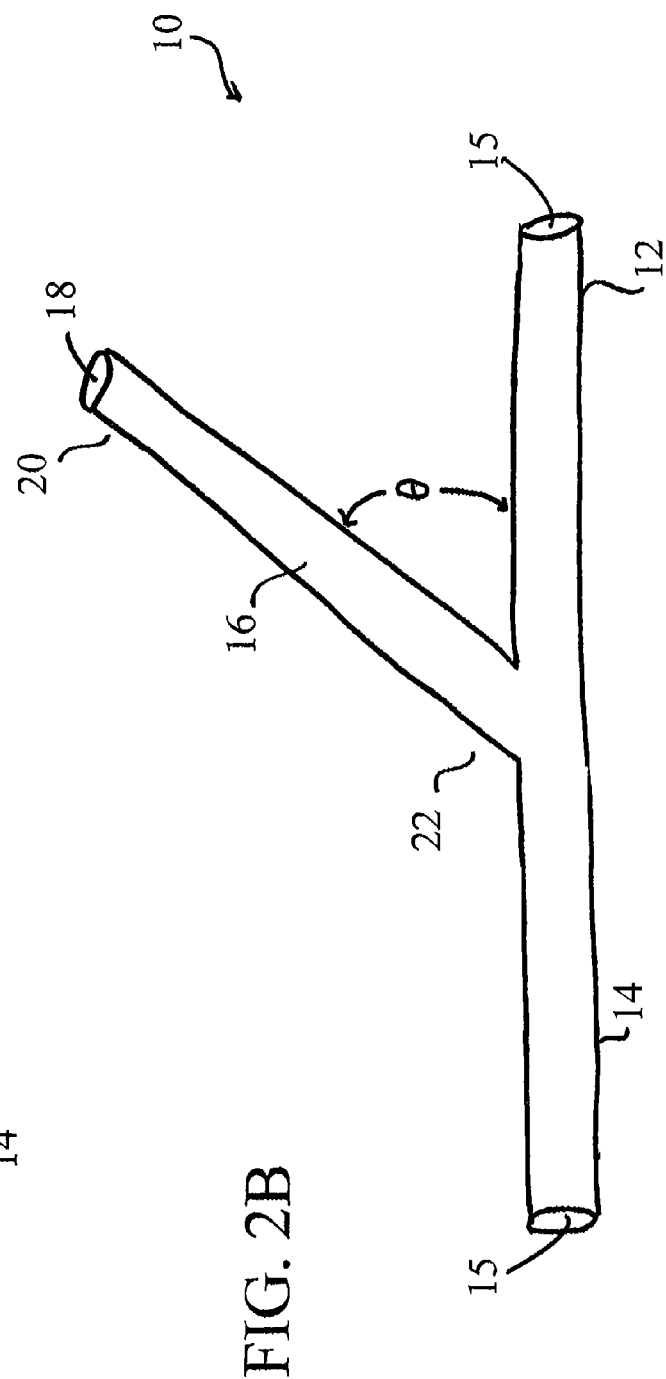
FIG. 2A
FIG. 2B

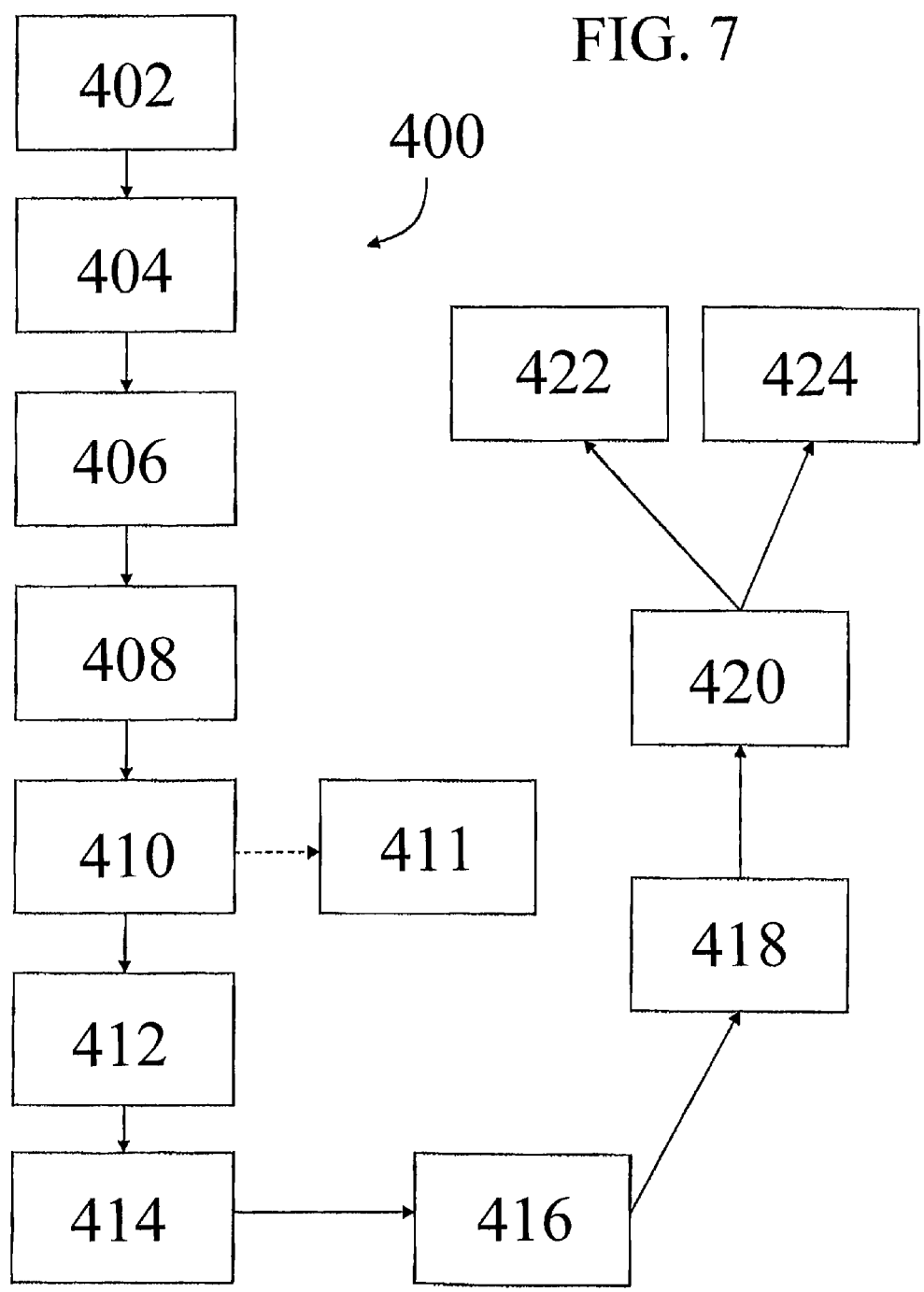

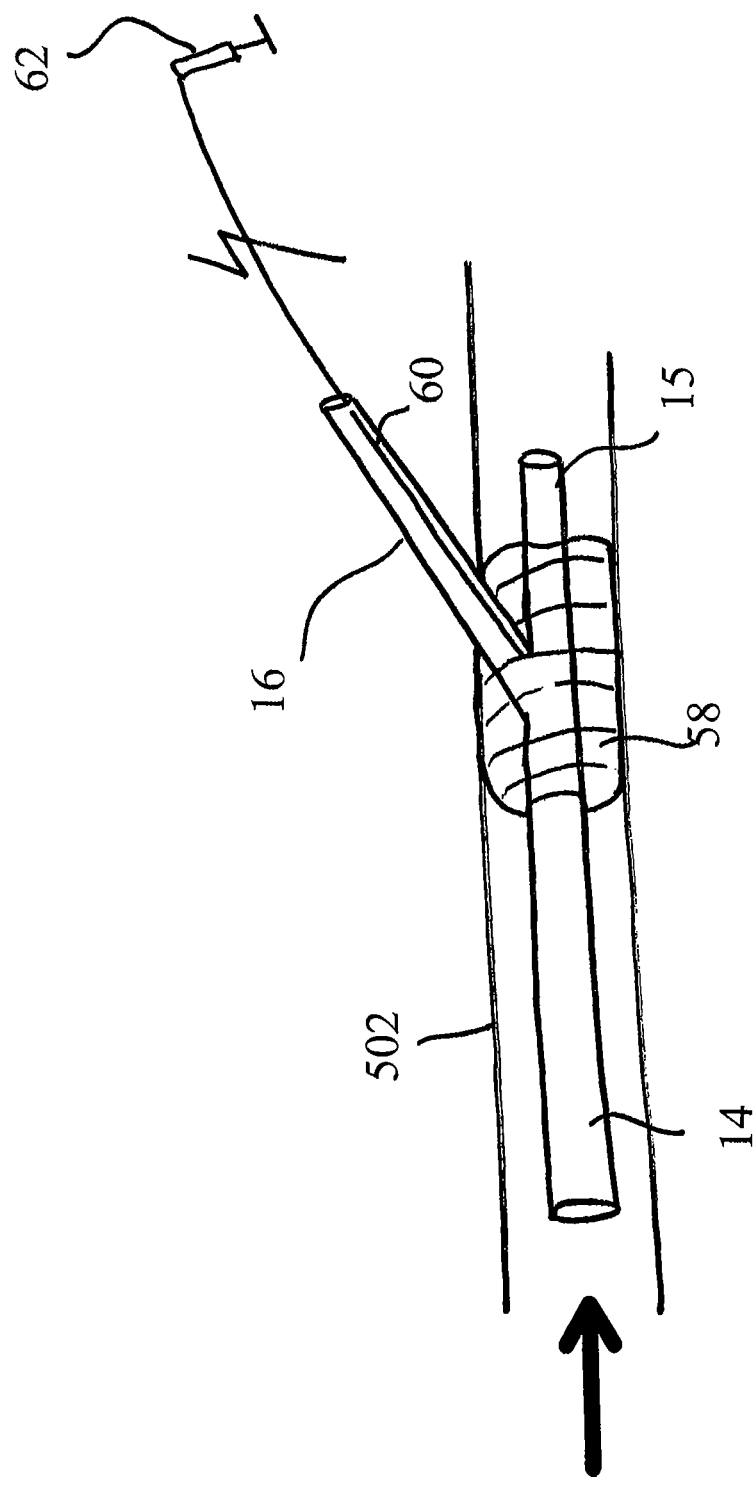

AUTORETROPERFUSION DEVICES AND SYSTEMS

PRIORITY

The present application is related to, and claims the priority benefit of, and is a U.S. §371 national stage entry of, International Patent Application Serial No. PCT/US2008/087863, filed Dec. 19, 2008, the contents of which are hereby incorporated by reference in their entirety into this disclosure.

BACKGROUND

While direct surgical and percutaneous revascularization through procedures such as a percutaneous transluminal coronary angioplasty ("PTCA") or coronary artery bypass grafting ("CABG") remain the mainstay of treatment for angina and coronary artery disease ("CAD"), there are many cardiac conditions that are not amendable to such conventional revascularization therapies. Because of this, much effort has been made to find alternative methods of revascularization for ischemic cardiac patients who are not candidates for revascularization by conventional techniques. Such patients are generally identified as "no-option" patients because there is no conventional therapeutic option available to treat their condition.

Currently, there are multiple specific conditions for which conventional revascularization techniques are known to be ineffective as a treatment. Two specific examples of such cardiac conditions include, without limitation, diffuse CAD and refractory angina. Furthermore, a percentage of all patients diagnosed with symptomatic CAD are not suitable for CABG or PTCA. In addition and for various reasons discussed below, diabetic patients—especially those with type 2 diabetes—exhibit an increased risk for having CAD that is not effectively treated by conventional revascularization techniques.

There is currently little data available on the prevalence and prognosis of patients with symptomatic CAD that is not amendable to revascularization through conventional methods. However, one study indicated that out of five hundred (500) patients with symptomatic CAD who were considering direct myocardial revascularization and angiogenesis, almost twelve percent (12%) were not suitable for CABG or PTCA for various reasons. Furthermore, in general, patients with atherosclerotic involvement of the distal coronary arteries have high mortality and morbidity. For example, a study conducted on patients indicated that, one (1) year after being diagnosed with atherosclerotic involvement of the distal coronary arteries, 39.2% of such patients had had a cardiac-related death, 37.2% had had an acute myocardial infarction, and 5.8% had developed congestive heart failure. Overall, 82.2% of the patients with atherosclerotic involvement of distal coronary arteries had developed or experienced a significant cardiac event within one (1) year.

A. Diffuse CAD and Refractory Angina

CAD is typically not focal (i.e. limited to one point or a small region of the coronary artery), but rather diffused over a large length of the entire vessel, which is termed "diffuse CAD." Several studies indicate that patients with a diffusely diseased coronary artery for whom standard CABG techniques cannot be successfully performed constitute about 0.8% to about 25.1% of all patients diagnosed with CAD. Furthermore, it is believed that diffuse CAD is much more common than conventionally diagnosed because it is often difficult to detect by an angiogram due to the two-dimensional views.

Practitioners have realized that the quality of a patient's distal coronary arteries is one of the critical factors related to a successful outcome of a surgical revascularization. As previously indicated, there is considerable evidence that CABG for vessels having diffuse CAD results in a relatively poor outcome. In fact, studies have indicated that diffuse CAD is a strong independent predictor of death after a CABG procedure. Further, as previously noted conventional revascularization techniques have also proven ineffective on a subgroup of patients with medically refractory angina. In line with the aforementioned reasoning, this is likely because patients with medically refractory angina have small or diffusely diseased distal vessels that are not amenable to conventional revascularization therapies. Accordingly, patients exhibiting diffuse CAD or medically refractory angina are often considered no-option patients and not offered bypass surgery, PCTA, or other conventional procedures.

B. Diabetes as a Risk Factor

Diabetes is an important risk factor for the development of CAD, diffuse or asymptomatic, and it has been estimated that approximately seventy-five percent (75%) of the deaths in diabetic patients are likely attributed to CAD. It is estimated that 16 million Americans have diabetes, with only 10 million being diagnosed. Patients with diabetes develop CAD at an accelerated rate and have a higher incidence of heart failure, myocardial infarction, and cardiac death than non-diabetics.

According to recent projections, the prevalence of diabetes in the United States is predicted to be about ten percent (10%) of the population by 2025. Further, the increasing prevalence of obesity and sedentary lifestyles throughout developed countries around the world is expected to drive the worldwide number of individuals with diabetes to more than 330 million by the year 2025. As may be expected, the burden of cardiovascular disease and premature mortality that is associated with diabetes will also substantially increase, reflecting in not only an increased amount of individuals with CAD, but an increased number of younger adults and adolescents with type 2 diabetes who are at a two- to four-fold higher risk of experiencing a cardiovascular-related death as compared to non-diabetics.

In addition to developing CAD at an accelerated rate, CAD in diabetic patients is typically detected in an advanced stage, as opposed to when the disease is premature and symptomatic. Consequently, when diabetic patients are finally diagnosed with CAD they commonly exhibit more extensive coronary atherosclerosis and their epicardial vessels are less amendable to interventional treatment, as compared to the non-diabetic population. Moreover, as compared with non-diabetic patients, diabetic patients have lower ejection fractions in general and therefore have an increased chance of suffering from silent myocardial infarctions.

C. No-Option Patients

Some studies have shown that two-thirds (⅔rds) of the patients who were not offered bypass surgery, because of diffuse CAD or otherwise, either died or had a non-fatal myocardial infarction within twelve (12) months. Furthermore, patients diagnosed with diffuse CAD ran a two-fold increased risk of in-hospital death or major morbidity, and their survival rate at two (2) years was worse than those patients who exhibited non-diffuse CAD or other complicating conditions. As previously indicated, the majority of these patients are considered no-option patients and are frequently denied bypass surgery as it is believed that CABG would result in a poor outcome.

Due to the increasing numbers of no-option patients and a trend in cardiac surgery towards more aggressive coronary interventions, a growing percentage of patients with diffuse CAD and other no-option indications are being approved for coronary bypass surgery because, in effect, there are no other meaningful treatment or therapeutic options. Some effects of this trend are that the practice of coronary bypass surgery has undergone significant changes due to the aggressive use of coronary stents and the clinical profiles of patients referred for CABG are declining. As such, performing effective and successful coronary bypass surgeries is becoming much more challenging. Bypass grafting diffusely diseased vessels typically requires the use of innovative operations such as on-lay patches, endarterectomies and more than one graft for a single vessel. Patients with "full metal jackets" (or multiple stents) are typically not referred to cardiac surgeons and often end up as no-option patients despite the attempts of using these innovative surgeries.

In recent decades, the spectrum of patients referred for CABG are older and are afflicted with other morbidities such as hypertension, diabetes mellitus, cerebral and peripheral vascular disease, renal dysfunction, and chronic pulmonary disease. In addition, many patients referred for CABG have advanced diffuse CAD and have previously undergone at least one catheter-based intervention or surgical revascularization procedure that either failed or was not effective. Because of this, the patient's vessels may no longer be graftable and complete revascularization using conventional CABG may not be feasible. An incomplete myocardial revascularization procedure has been shown to adversely affect short-term and long-term outcomes after coronary surgery.

Due in part to some of the aforementioned reasons, reoperative CABG surgery is now commonplace, accounting for over twenty percent (20%) of cases in some clinics. It is well established that mortality for reoperative CABG operations is significantly higher than primary operations. As such, the risk profile of reoperative patients is significantly increased and such patients are subjected to an increased risk of both in-hospital and long-term adverse outcomes.

Further, clinicians have also turned to unconventional therapies to treat non-option patients. For example, coronary endarterectomy ("CE") has been used as an adjunct to CABG in a select group of patients with diffuse CAD in order to afford complete revascularization. However, while CE was first described in 1957 as a method of treating CAD without using cardiopulmonary bypass and CABG, this procedure has been associated with high postoperative morbidity and mortality rates and has been afforded much scrutiny. Nevertheless, CE is the only therapeutic option available for many no-option patients with diffuse CAD.

Similarly, because conventional therapies have proven ineffective or are unavailable to high risk patients, perioperative transmyocardial revascularization ("TMR") has been indicated for patients suffering from medically refractory angina. TMR has proven effective for most patients suffering from refractory angina; the mortality rate after TMR in patients with stable angina ranges between about one to twenty percent (1-20%). Furthermore, in one study, TMR resulted in a higher preoperatively mortality rate in patients with unstable angina than those with stable angina (27% versus 1%). Some even report an operative mortality rate as low as twelve percent (12%). Patients who experience angina and who cannot be weaned from intravenous nitroglycerin and heparin have a significantly higher operative mortality rate (16-27% versus 1-3%). Based on these findings, the clinical practice has been to avoid taking such patients to the operating room for TMR if at all possible. The success of TMR is thought to be due to improved regional blood flow to ischemic myocardium, but the precise mechanisms of its effects remain unclear.

BRIEF SUMMARY

Disclosed herein are the devices, systems and methods for providing controlling blood perfusion pressure and/or providing retroperfusion to at least one ischemic tissue in a minimally invasive manner. At least some of the disclosed embodiments enable an anastomosis to be formed between a vein and an artery without the use of sutures and through a non-invasive procedure. In addition, various disclosed embodiments provide a cannula device comprising a Y-configuration for bifurcating the arterial flow between an anastomosis and the underlying artery. Examples of the devices, systems and methods described herein can further provide simultaneous autoretroperfusion therapy to more than one area of an ischemic tissue.

In at least one embodiment of a catheter for controlling blood perfusion pressure, the catheter comprises an elongated body having a proximal open end, a distal open end, at least one lumen extending between the proximal open end and the distal open end, and a cannula having a hollow interior. In this at least one embodiment, the hollow interior of the cannula is in fluid communication with at least one of the at least one lumens of the elongated body, and the cannula extends from the elongated body such that an angle is formed therebetween. The elongated body of the catheter may be configured for placement within an arterial vessel or any other vessel of interest. The hollow interior of the cannula may further comprise a first diameter and the at least one lumen of the elongated body may further comprise a second diameter. In at least one example, the first diameter of the hollow interior of the cannula is less than the second diameter of the at least one lumen of the elongated body. However, it will be understood that the hollow interior of the cannula may comprise any diameter and, in at least one embodiment, the hollow interior of the cannula is between about 2.7 millimeters to about 4 millimeters in diameter.

The cannula of the catheter may also be moveable between a substantially extended configuration and a substantially collapsed configuration. Here, the substantially extended configuration may comprise any angle between about 15° and about 90° and the substantially collapsed configuration may comprise any angle that is less than about 15°. In at least one example of the cannula, the cannula is biased towards the substantially extended configuration.

The catheter described herein may further comprise an expandable balloon coupled with the elongated body of the catheter in a position adjacent to where the cannula extends from the elongated body. The expandable balloon may comprise any configuration and, in at least one embodiment, is configured to prevent fluid leakage through an arterial opening when the expandable balloon is in a substantially inflated configuration and the elongated body of the catheter is positioned within an arterial vessel such that the cannula extends through the arterial opening. In this at least one embodiment, the catheter may also comprise a balloon port and a secondary lumen. Here, the balloon port may be in fluid communication with the expandable balloon through a secondary lumen of the catheter. The balloon port may be configured for subcutaneous implantation on a patient or otherwise.

In a yet another example of the catheter described herein, the catheter may comprise an elongated body for placement within a vessel and having a proximal end, a distal end. In addition, the catheter may comprise at least one lumen extending between the proximal end and the distal end of the elongated body. Here, the distal end of the catheter may be configured to receive a fluid flowing through the vessel and the proximal end of the catheter may be configured to allow the fluid received by the distal end of the elongated body to flow from the at least one lumen of the catheter therethrough. In addition, the catheter may comprise a cannula extending from the elongated body such that an angle is formed between the cannula and the elongated body. The cannula may comprise a hollow interior that is in fluid communication with the at least one of the at least one lumens of the elongated body and be configured to route a portion of the fluid received by the distal end of the elongated body outside of the vessel. In at least one embodiment of the catheter, the vessel that the elongated body is configured for placement in comprises an artery.

Systems are also disclosed herein for controlling blood perfusion pressure within a vein. In at least one embodiment, a system may comprise a first catheter for placement within an arterial vessel, a second catheter for placement within a venous vessel and a connector. The distal end of the second catheter may further comprise at least one sensor capable of monitoring a condition within a venous vessel. In at least one embodiment of this system, the first catheter may comprise embodiments of the catheter previously described herein. Further, the second catheter may comprise a proximal end, a distal end, and at least one lumen extending between the proximal end and the distal end. In this at least one embodiment, the connector is coupled with the cannula of the first catheter and the proximal end of the second catheter. In addition, embodiments of the connector may comprise a means for measuring data associated with the fluid flowing from the first catheter to the second catheter through the connector. In certain embodiments, the fluid of the system comprises arterial blood. In this manner, the system described herein can form an anastomosis between an arterial vessel and a venous vessel such that arterial blood can flow therethrough.

Additionally, in at least some embodiments, the second catheter may comprise an expandable balloon coupled with the exterior of the distal end of the second catheter. The at least one lumen of the second catheter of the system may further comprise at least one primary lumen and at least one secondary lumen. Here, for example, the expandable balloon may be in fluid communication with the at least one secondary lumen of the second catheter. Additionally, the system may further comprise a balloon port in fluid communication with the expandable balloon of the second catheter through the at least one secondary lumen.

In yet another at least one embodiment of the system, the system may further comprise a stenosis positioned within the at least one primary lumen of the second catheter. In this manner, the stenosis can affect the pressure of the fluid flowing through the primary lumen of the catheter. In at least one embodiment, the stenosis may comprise an expandable balloon. In such an embodiment, the at least one lumen of the second catheter may also further comprise a tertiary lumen in fluid communication with the expandable balloon positioned within the primary lumen of the second catheter. Still further, the system may comprise a balloon port in fluid communication with the expandable balloon positioned within the primary lumen of the second catheter through the tertiary lumen of the second catheter.

In yet another at least one embodiment, the second catheter of the system may further comprise an expandable balloon coupled therewith. Where the system comprises a first expandable balloon coupled with the primary lumen of the second catheter and a second expandable balloon coupled with the second catheter, the first and second expandable balloons of the second catheter may be capable of being inflated and deflated independently of each other through respective balloon ports coupled therewith. Accordingly, a clinician can independently control each expandable balloon coupled with the second catheter.

The systems described herein may further comprise a first graft coupled with the proximal end of the second catheter and the connector such that the at least one lumen of the second catheter is in fluid communication with the at least one lumen of the first catheter. In this manner, the first graft may be used to form a portion of the anastomosis formed between the arterial vessel and the venous vessel. Alternatively, a second graft may also be coupled with the cannula of the first catheter and the connector such that the at least one lumen of the second catheter is in fluid communication with the at least one lumen of the first catheter. In yet another at least one embodiment, the system may comprise both a first graft and a second graft, wherein the first graft is coupled with the cannula of the first catheter and the connector, and the second graft is coupled with the cannula of the first catheter and the connector such that the at least one lumen of the second catheter is in fluid communication with the at least one lumen of the first catheter.

As previously described, the controller of the system may comprise a means for measuring data associated with fluid flowing therethrough and/or may simply be capable of measuring data associated with fluid flowing therethrough. In addition, the system may further comprise a remote module either in direct or wireless communication with the controller and/or the means for measuring data. In at least some embodiments, the remote module may be capable of receiving the data measured by the connector, either through wired transmission, wireless communication (for example and without limitation through telemetry, radio waves, or wireless internet), or other transmission means known in the art. Here, the means for measuring data and/or the controller may be capable of transmitting the data collected to the remote module either through wired transmission, wireless communication, or other transmission means known in the art.

Other examples of the controller of the system described herein may further comprise a means for regulating blood flow and/or may simply be capable of regulating blood flow. In such examples, the remote module may be capable of adjusting the means for regulating blood flow either wirelessly, through wired transmission, or otherwise. As such, the remote module may be able to communicate with the controller, either wirelessly or otherwise, such that it can adjust the controller to regulate the blood flow flowing therethrough pursuant to a set of instructions.

The system described herein may further comprise at least one guidewire having a proximal end and a distal end. In at least one embodiment, the at least one guidewire is capable of being slidably inserted within the at least one lumen of the second catheter. Furthermore, the distal end of the at least one guidewire further comprises a plurality of electrodes disposed thereon. In certain embodiments, the plurality of electrodes may comprise a combination of excitation and detection electrodes for use in determining the cross-sectional area of a vessel.

In other embodiments, the system described herein may further comprise a third catheter for placement within a venous vessel adjacent to the second catheter described above. The third catheter may comprise a proximal end, a distal end, and at least one lumen extending between the proximal end and the distal end. Furthermore, in certain embodiments, the third catheter may be configured identically to the embodiments of the second catheter described above. In addition to the third catheter, at least one embodiment of the system may further comprise a Y-connector configured for placement within the venous vessel. The Y-connector may comprise an open proximal end, a distal end having at least two branches, and a lumen extending between the open proximal end and bifurcating between the at least two branches of the distal end, the open proximal end of the Y-connector coupled with the connector, one of the at least two branches of the distal end coupled with the proximal end of the second catheter, and one of the at least two branches of the distal end coupled with the proximal end of the third catheter such that the at least one lumen of the second catheter and the at least one lumen of the third catheter are in fluid communication with the at least one lumen of the first catheter.

In at least one method for arterializing a vein, the method comprises the steps of: providing the system described above; introducing the distal end of the first catheter into an artery through an arterial opening such that a first amount of arterial blood flows through the at least one lumen of the elongated body of the first catheter, the cannula extends through the arterial opening, and a second amount of arterial blood flows through the cannula of the first catheter; introducing the distal end of the second catheter into a vein to be arterialized; and forming an anastomosis between the artery and the vein by coupling the connector with the cannula of the first catheter and the proximal end of the second catheter. The method may also further comprise the step of decreasing the pressure of the amount of arterial blood flowing through the cannula of the first catheter prior to allowing the amount of arterial blood to flow into the vein to be arterialized through the distal end of the second catheter. Furthermore, the step of introducing the distal end of the first catheter into an artery further comprises the steps of: providing an introducer having a proximal end, a sharp distal end and a hollow interior extending between the proximal end and the sharp distal end, the first catheter slidably disposed in the substantially collapsed configuration within the hollow interior of the introducer; puncturing the artery with the sharp distal end of the introducer to create an arterial opening; advancing the sharp distal end of the introducer through the arterial opening and into the lumen of the artery; withdrawing the sharp distal end of the introducer through the arterial opening such that the elongated body of the first catheter remains within the lumen of the artery; retaining the cannula of the first catheter within the hollow interior of the introducer; and withdrawing the sharp distal end of the introducer such that the cannula is released from the hollow interior of the introducer in the substantially extended configuration and extends through the arterial opening. In yet another at least one embodiment, the step of introducing the distal end of the first catheter into an artery further comprises the step of inflating the first expandable balloon to anchor the elongated body of the first catheter within the artery and prevent leakage through the arterial opening.

In yet another embodiment of the method described herein, the step of introducing the distal end of the second catheter into a vein to be arterialized further comprises the steps of: providing a delivery catheter and a guidewire, the delivery catheter comprising a proximal end, a distal end, and a hollow interior extending between the distal end and the proximal end and capable of slidably receiving at least the second catheter and the guidewire therein, and the guidewire comprising a proximal end and a distal end; introducing the delivery catheter into the lumen of the vein; advancing the distal end of the delivery catheter to or near a targeted location within the lumen of the vein; introducing the guidewire into the hollow interior of the delivery catheter; advancing the distal end of the guidewire into the lumen of the vein through the distal end of the delivery catheter; and advancing the distal end of the second catheter into the lumen of the vein and to a location at or near the targeted location by threading the distal end second catheter over the guidewire. In addition, the method may further comprise the step of inflating the expandable balloon to anchor the distal end of the second catheter within the lumen of the vein at or near the targeted location and/or the step of measuring the cross-sectional area of the lumen of the vein in the targeted location.

The method described herein may further comprise additional steps directed towards decreasing the pressure of the arterial blood flowing through the cannula of the first catheter. In at least one embodiment, the step of decreasing the pressure of the amount of arterial blood flowing through the cannula of the first catheter prior to allowing the arterial blood to flow into the vein to be arterialized through the distal end of the second catheter comprises positioning a stenosis within the at least one lumen of the second catheter to partially occlude the same. In at least one embodiment, the stenosis comprises an expandable balloon. In yet another at least one embodiment, the stenosis comprises a resorbable stenosis. Furthermore, in at least one embodiment of the method, the at least one lumen of the first catheter of the system may comprise a first diameter and the hollow interior of the cannula of the first catheter of the system comprises a second diameter, wherein the second diameter is less than the first diameter such that a difference in pressure is achieved between the arterial blood flowing through the elongated body of the first catheter and the arterial blood flowing through the hollow interior of the cannula. In other embodiments of the method described herein, the controller of the system may comprise a means for regulating blood flow and the step of decreasing the pressure of the amount of arterial blood flowing through the cannula of the first catheter prior to allowing the arterial blood to flow into the vein to be arterialized through the distal end of the second catheter may comprise adjusting the means for regulating blood flow.

Methods for simultaneously arterializing at least two venous branches are also described, with at least one embodiment of the method comprising the steps of: providing at least one embodiment of the system described above; introducing the distal end of the first catheter into an artery such that a first amount of arterial blood flows through the elongated body of the first catheter and a second amount of arterial blood can flow through the cannula of the first catheter; introducing the distal end of the second catheter into a first venous branch of a vein to be arterialized; introducing the distal end of the third catheter into a second venous branch of the vein to be arterialized; introducing the distal end of the Y-connector into the vein; and forming an anastomosis between the artery and the vein by coupling the connector with the cannula of the first catheter and the proximal end of the Y-connector. Further, the method may further comprise the step of decreasing the pressure of the amount of arterial blood flowing through the cannula of the first catheter prior to allowing the amount of arterial blood to flow into the first venous branch through the distal end of the second catheter or into the second venous branch through the distal end of the third catheter. In addition, at least one embodiment of the method may comprise the step of introducing the distal end of the first catheter into an artery further comprises the steps of: providing an introducer having a proximal end, a sharp distal end and a hollow interior extending between the proximal end and the sharp distal end, the first catheter slidably disposed in the substantially collapsed configuration within the hollow interior of the introducer; puncturing the artery with the sharp distal end of the introducer to create an arterial opening; advancing the sharp distal end of the introducer through the arterial opening and into the lumen of the artery; withdrawing the sharp distal end of the introducer through the arterial opening such that the elongated body of the first catheter remains within the lumen of the artery; retaining the cannula of the first catheter within the hollow interior of the introducer; and withdrawing the sharp distal end of the introducer such that the cannula is released from the hollow interior of the introducer in the substantially extended configuration and extends through the arterial opening.

Furthermore, in yet another at least one embodiment, the method for simultaneously arterializing at least two venous branches may further comprise the steps of introducing the distal end of the second catheter into a first venous branch of a vein to be arterialized and introducing the distal end of the third catheter into a second venous branch of the vein to be arterialized further comprise the steps of: providing a delivery catheter, a first guidewire, and a second guidewire, the delivery catheter comprising a proximal end, a distal end, and a hollow interior extending between the distal end and the proximal end and capable of slidably receiving at least the second catheter and the guidewire therein, and the first and second guidewires each comprising a proximal end and a distal end; introducing the distal end of the delivery catheter into the lumen of the vein; advancing the distal end of the delivery catheter to or near a targeted location within the lumen of the vein; introducing the first guidewire into the delivery catheter; advancing the distal end of the first guidewire through the distal end of the delivery catheter to a targeted location within the first venous branch of the vein; advancing the distal end of the second catheter over the first guidewire and through the hollow interior of the delivery catheter; advancing the distal end of the second catheter through the distal end of the delivery catheter to the targeted location within the first venous branch of the vein; introducing the second guidewire into the delivery catheter; advancing the distal end of the second guidewire through the distal end of the delivery catheter to a targeted location within the second venous branch of the vein; advancing the distal end of the third catheter through the hollow interior of the delivery catheter over the second guidewire; and advancing the distal end of the third catheter through the distal end of the delivery catheter to the targeted location within the second venous branch of the vein. In yet another embodiment of the methods described herein, the first catheter of the system further comprises an expandable balloon coupled with the elongated body in a location adjacent to the cannula, and wherein the step of introducing the distal end of the first catheter into an artery further comprises the step of inflating the first expandable balloon to anchor the elongated body of the first catheter within the artery and to prevent leakage through the arterial opening. In addition, the second catheter of the system may further comprise a first expandable balloon coupled with the exterior of the distal end of the second catheter and the third catheter of the system further comprises a second expandable balloon coupled with the exterior of the distal end of the third catheter, and further comprising the steps of: inflating the first expandable balloon to anchor the distal end of the second catheter at the targeted location within the first venous branch of the vein; inflating the second expandable balloon to anchor the distal end of the third catheter at the targeted location within the second venous branch of the vein; and withdrawing the first and second guidewires and the delivery catheter from the vein. In yet another embodiment of the method, the method may further comprise the steps of: measuring the cross-sectional area of the first venous branch of the vein; and measuring the cross-sectional area of the second venous branch of the vein. Embodiments of the method may additionally comprise the step of sizing the first and second expandable balloons respectfully based on the measurements of the first and second venous branches. Still further, in at least one embodiment of the method, the step of decreasing the pressure of the amount of the amount of arterial blood flowing through the cannula of the first catheter prior to allowing the amount of arterial blood to flow into the first venous branch through the distal end of the second catheter or into the second venous branch through the distal end of the third catheter comprises the steps of: positioning a first stenosis within the at least one lumen of the second catheter to partially occlude the same; and positioning a second stenosis within the at least one lumen of the third catheter to partially occlude the same. In yet another at least one embodiment of the method, the controller of the system further comprises a means for regulating blood flow and wherein the step of decreasing the pressure of the amount of the amount of arterial blood flowing through the cannula of the first catheter prior to allowing the amount of arterial blood to flow into the first venous branch through the distal end of the second catheter or into the second venous branch through the distal end of the third catheter comprises adjusting the means for regulating blood flow.

Kits are also described herein for performing a medical procedure. In at least one embodiments, such kits may comprise a first catheter for placement within an arterial vessel, the first catheter comprising an elongated body having a proximal open end, a distal open end, at least one lumen extending between the proximal open end and the distal open end, and a cannula having a hollow interior that is in fluid communication with at least one of the at least one lumens of the elongated body, and the cannula extends from the elongated body such that an angle is formed therebetween; a second catheter for placement within a venous vessel, the second catheter having a proximal end, a distal end, and at least one lumen extending between the proximal end and the distal end; a connector coupled with the cannula of the first catheter and the proximal end of the second catheter, the connector comprising a means for measuring data associated with fluid flowing therethrough; an introducer for delivering the first catheter into the arterial vessel, the introducer having a proximal end, a sharp distal end and a hollow interior, the hollow interior capable of slidably receiving the first catheter therein; at least one guidewire; and a delivery catheter for delivering at least the second catheter into the venous vessel, the delivery catheter comprising a proximal end, a distal end, and a hollow interior capable of slidably receiving the at least one guidewire and the second catheter therein. Such a kit may also comprise a third catheter for placement within the venous vessel, the third catheter having a proximal end, a distal end, and at least one lumen extending between the proximal end and the distal end; and a Y-connector configured for placement within the venous vessel and having an open proximal end, a distal end having at least two branches, and a lumen extending between the open proximal end and bifurcating between the at least two branches of the distal end, one of the at least two branches of the distal end coupled with the proximal end of the second catheter, and one of the at least two branches of the distal end coupled with the proximal end of the third catheter. Furthermore, a kit as described herein my further comprise at least one graft.

BRIEF DESCRIPTION OF THE DRAWINGS

FIG. 2A shows a side view of the catheter of FIG. 1 in a collapsed position.

FIG. 2B shows a side view of the catheter of FIG. 1 in an extended position.

FIG. 7 shows a flow chart of a method for delivering autoretroperfusion therapy.

FIG. 8E shows a side view of the catheter of FIG. 1 anchored within an arterial vessel through the use of an expandable balloon.

DETAILED DESCRIPTION

It will be appreciated by those of skill in the art that the following detailed description of the disclosed embodiments is merely exemplary in nature and is not intended to limit the scope of the appended claims. The embodiments discussed herein include devices, systems, and methods useful for providing selective autoretroperfusion to the venous system and simultaneously achieving the controlled arterialization of the venous system. The devices, systems and methods disclosed herein can be used to safely and selectively arterialize venous vessels in order to decrease the stress thereon and prevent rupture of the same. Accordingly, through the use of the devices, systems and methods disclosed herein, long-term autoretroperfusion of oxygenated blood through the coronary venous system can be achieved, thereby providing a continuous supply of oxygen-rich blood to an ischemic area of a tissue or organ. While the devices, systems and methods disclosed herein are described in connection with a heart, it will be understood that such devices, systems and methods are not limited in their application solely to the heart and the same may be used in connection with any ischemic tissue and/or organ in need of an oxygen-rich blood supply.

Figure 1:
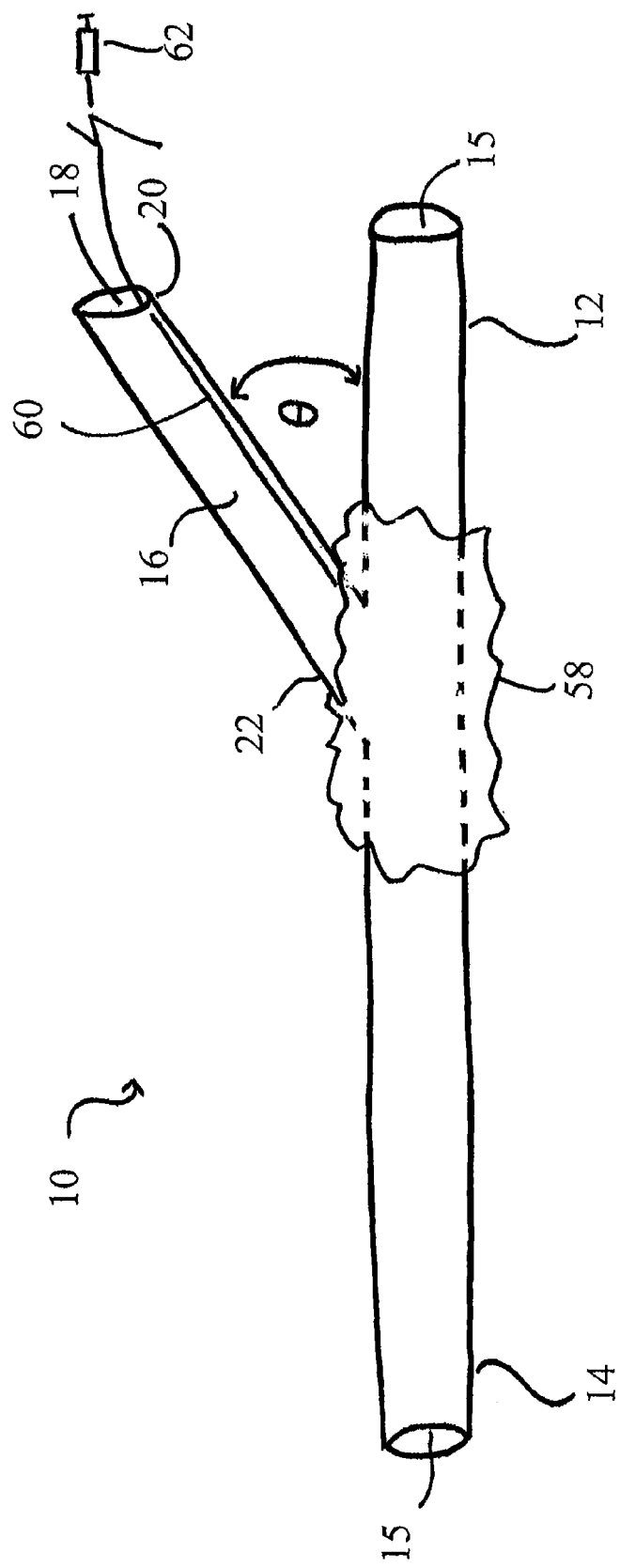
FIG. 1 shows a side view of a catheter for placement within an arterial vessel and that may be used to deliver retroperfusion therapy.

Now referring to FIG. 1, a side view of a catheter 10 is shown. The catheter 10 is configured to be placed within an arterial vessel and comprises a flexible, elongated tube having a proximal end 12, a distal end 14 and at least one lumen 15 extending between the proximal end 12 and the distal end 14. The dimensions of the catheter 10 may vary depending on the particulars of a specific patient or with respect to the artery to be cannulated. For example and without limitation, where the catheter 10 is used to in a system for autoretroperfusion of the coronary sinus, the catheter 10 may comprise a diameter of about 2.7 millimeters to about 4 millimeters (about 8 Fr to about 12 Fr). Furthermore, the at least one lumen 15 of the catheter 10 comprises a sufficient diameter such that blood can flow therethrough. In addition, the catheter 10 may be comprised of any appropriate material, including without limitation, polyurethane or silicone rubber. Furthermore, the catheter 10 may be coated with heparin or any other suitable anti-coagulant such that the catheter 10 may be placed within a vessel for an extended period of time without inhibiting blood flow due to coagulation.

The distal end 14 of the catheter 10 is configured to allow arterial blood to flow therethrough and into the at least one lumen 15 of the catheter 10. Similarly, the proximal end 12 of the catheter 10 is configured to allow blood within the at least one lumen 15 to flow out of the catheter 10. Accordingly, when the catheter 10 is positioned within an arterial vessel, the oxygenated blood is allowed to flow into the catheter 10 through the distal end 14 of the catheter 10, through the at least one lumen 15, and out of the catheter 10 through the proximal end 12 of the catheter 10. In this manner, placement of the catheter 10 within a vessel does not inhibit the flow of blood through the vessel or significantly affect the pressure of the blood flow within the vessel.

As shown in FIG. 1, the catheter 10 further comprises a projection cannula 16 that extends from the proximal end 12 of the catheter 10 and forms a Y-shaped configuration therewith. The projection cannula 16 comprises a flexible tube of material that is appropriate for insertion within a vessel and placement within an opening in a vessel wall. Furthermore, the projection cannula 16 comprises at least one lumen 18, a proximal end 20, and a distal end 22. The distal end 22 of the projection cannula 16 is coupled with the body of the catheter 10 and configured to allow the lumen 18 of the projection cannula 16 to communicate with at least one of the at least one lumens 15 of the catheter 10. Accordingly, when blood flows through the at least one lumen of the catheter 10, a portion of the blood flow enters the lumen 18 of the projection cannula 16 through the distal end 22 thereof and flows out through the proximal end 20 of the projection cannula 16. In this manner, the catheter 10 is capable of bifurcating the flow of blood through the vessel in which it is inserted and routing some of that blood flow out of the vessel and to another location.

This bifurcation can be exploited to modify the pressure of the blood flowing through the projection cannula 16 and/or through the proximal end 12 of the catheter 10 by manipulating the dimensions of the projection cannula 16 and the body of the catheter 10. For example, and without limitation, if the diameter of the projection cannula 16 is less than the diameter of the at least one lumen 15 of the catheter 10, the majority of the blood will flow through the proximal end 12 of the catheter 10 and the pressure of the remaining blood that flows through the smaller projection cannula 16 will necessarily be reduced. Predictably, the smaller the diameter of the lumen 18 of the projection cannula 16, the greater the pressure drop that can be achieved in the blood flowing through the lumen 18 of the projection cannula 16. Accordingly, with respect to the catheter's 10 application to autoretroperfusion therapies, the projection cannula 16 can be used to re-route blood flow from an artery to a vein while simultaneously achieving the necessary pressure drop in the re-routed blood between the arterial system and unarterialized venous system. Moreover, the catheter 10 is capable of maintaining substantially normal blood flow through the artery in which it is housed as the arterial blood not re-routed through the projection cannula 16 is allowed to flow through the open proximal end 12 of the catheter 10 and back into the artery in the normal antegrade fashion.

Due to the configuration of the projection cannula 16 and the material of which it is comprised, the projection cannula 16 is capable of hingedly moving relative to the body of the catheter 10 between a collapsed position and an extended position. Now referring to FIGS. 2A and 2B, the projection cannula 16 is shown in the collapsed position (FIG. 2A) and in the extended position (FIG. 2B). When the projection cannula 16 is in the collapsed position, the projection cannula 16 is positioned substantially parallel with the body of the catheter 10. Alternatively, when the projection cannula 16 is in the extended position, the projection cannula 16 is positioned such that the projection cannula 16 forms an angle θ with the proximal end 12 of the catheter 10. The value of angle θ may be selected depending on the desired application of the catheter 10. For example, in at least one embodiment, the angle θ may comprise any value ranging between about 15° and about 90°. In another example, the angle θ may comprise about 45° when the projection cannula 16 is in the extended position.

The projection cannula 16 is biased such that, when it is not subject to a downward force, the projection cannula 16 rests in the expanded position. Conversely, when a downward force is applied to the projection cannula 16 by way of an introducer or otherwise, the projection cannula 16 moves into and remains in the collapsed position until the downward force is removed. In this manner, the projection cannula 16 may be introduced into a vessel in the collapsed position through the use of an introducer or shaft and thereafter move into the expanded position when the catheter 10 is properly positioned within the vessel and the introducer or shaft is removed.

Optionally, as shown in FIG. 1, the catheter 10 may further comprise an expandable balloon 58 coupled with an intermediary portion of the external surface of the catheter 10 such that the expandable balloon 58 encases the catheter 10 and the distal end 22 of the projection cannula 18. The expandable balloon 58 may be any expandable balloon 58 that is appropriate for insertion within a vessel and may comprise any material suitable for this function, including without limitation, polyethylene, latex, polyestherurethane, polyurethane, sylastic, silicone rubber, or combinations thereof. In operation, the expandable balloon 58 can be used to anchor the catheter 10 in a desired position within a vessel wall and prevent leakage from the opening in the vessel wall through which the projection cannula 16 traverses.

The expandable balloon 58 is capable of being controlled by a clinician such that it can inflate and/or deflate to the proper size. The sizing of the expandable balloon 58 will differ between patients and applications. The expandable balloon 58 may be in fluid communication with a balloon inflation port 62 through a secondary lumen 60 within the lumen 18 of the projection cannula 16. Alternatively, the expandable balloon 58 may be in fluid communication with the balloon inflation port 62 through a tube or other means that is positioned within the lumen 18 of the projection cannula 16 as shown in FIG. 1. The balloon port 62 may be positioned subcutaneously or otherwise such that a clinician can easily access the balloon port 62 when the catheter 10 is positioned within a vessel. In this manner the balloon port 62 can be accessed by a clinician, subcutaneously, percutaneously or otherwise, and used to inflate or deflate the expandable balloon 58 with no or minimal invasion to the patient.

Figure 3:
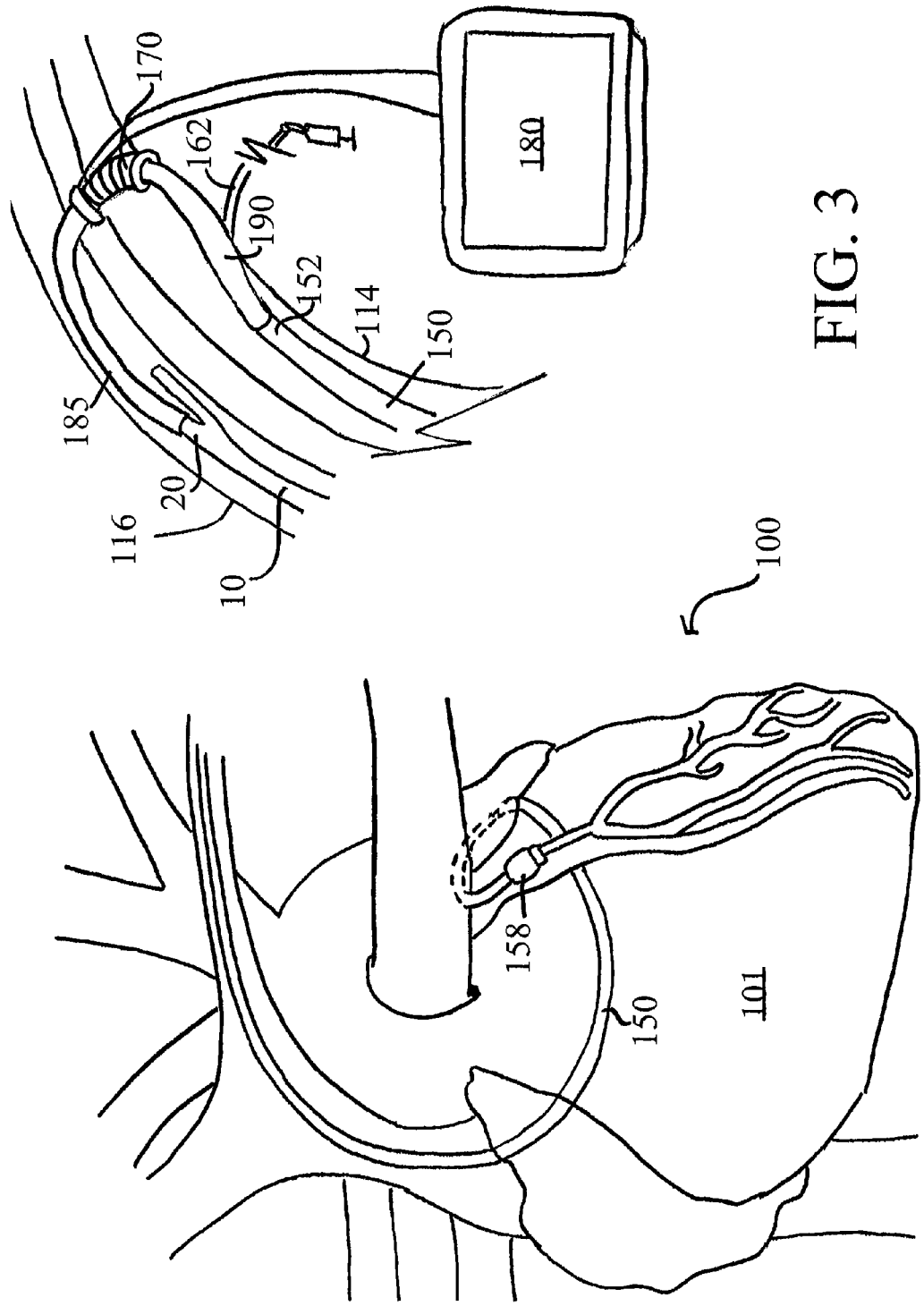
FIG. 3 shows a side view of an autoretroperfusion system positioned to deliver retroperfusion therapy to a heart.

Now referring to FIG. 3, an autoretroperfusion system 100 is shown positioned to allow arterial blood to irrigate the coronary sinus of a heart 101. With respect to the heart 101, the autoretroperfusion system 100 may be used for treatment of myocardial infarctions by injecting arterial blood into the coronary sinus in synchronism with the patient's heartbeat. Furthermore, the autoretroperfusion system 100 is capable of controlling the pressure of the arterial blood flow as it enters the venous vessel such that when the arterial blood flow is first introduced into the venous system, the pressure of the re-routed arterial blood flow is reduced to protect the thinner venous vessels. In this manner, the venous system is allowed to gradually arterialize. Further, after the selected venous vessel has sufficiently arterialized, the autoretroperfusion system 100 is capable of reducing or ceasing its influence on the pressure of the re-routed arterial blood flow such that the standard arterial blood flow pressure is thereafter allowed to flow into the arterialized venous vessel.

Autoretroperfusion system 100 comprises the catheter 10, a second catheter 150, and a connector 170. The catheter 10 is for placement within an arterial vessel and is configured as previously described in connection with FIGS. 1-2B. The second catheter 150 is configured for placement within the venous system. The connector 170 is configured to form an anastomosis between the catheter 10 and the second catheter 150 and further functions to monitor various data points on the blood flow flowing therethrough. In addition, in at least one embodiment, the connector 170 is capable of controlling the pressure of arterial blood flowing therethrough.

The second catheter 150 is configured for placement within a venous vessel wall 114 and comprises a flexible tube having a proximal end 152, a distal end 154 and at least one lumen 156 extending between the proximal end 152 and the distal end 154. Both the proximal end 152 and the distal end 154 of the second catheter 150 are open and in communication with the at least one lumen 156 of the second catheter 150, thereby allowing blood to flow into the at least one lumen 156 through the proximal end 152 and out of the distal end 154 back into the venous vessel 114. The second catheter 150 may be any catheter known in the art that is capable of intravascular insertion and advancement through the venous system and may comprise any appropriate material, including without limitation, polyurethane or silicone rubber. In at least one embodiment, the second catheter 150 is configured to receive a guidewire 510 (see FIGS. 4A and 4B) through the at least one lumen 156 to facilitate the intravascular delivery of the distal end 154 of the second catheter 150 into the desired location of the venous vessel 114. Furthermore, similar to the catheter 10, the second catheter 150 may be coated with heparin or any other suitable anti-coagulant prior to insertion in order to facilitate the extended placement of the second catheter 150 within the venous vessel 114. Accordingly, the autoretroperfusion system 100 may be used to deliver chronic retroperfusion treatment to an ischemic area of a body.

Figure 4:
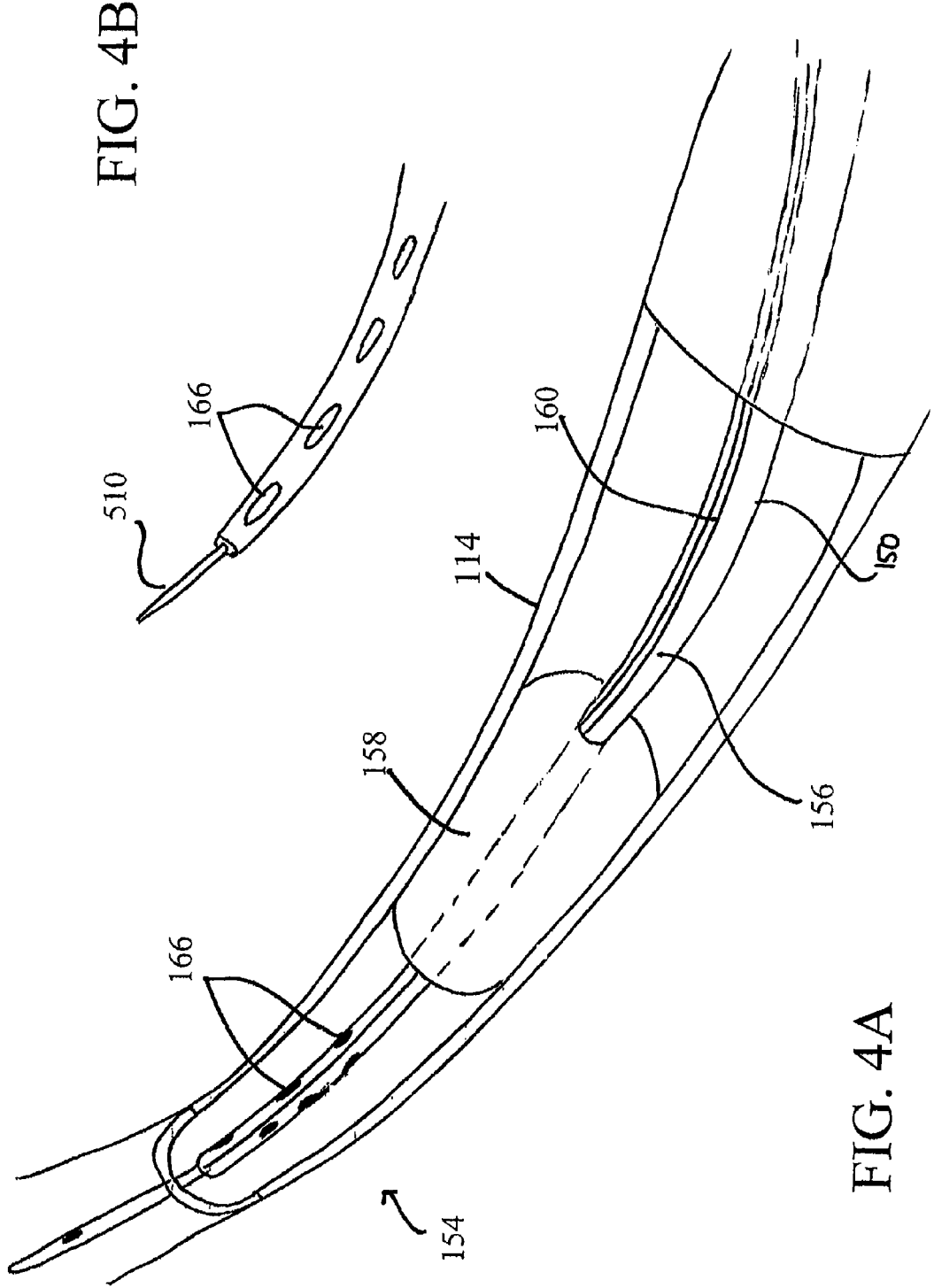
FIGS. 4A and 4B show perspective views of the distal end of a venous catheter used in the autoretroperfusion system of FIG. 3.

FIGS. 4A and 4B show side views of the distal end 154 of the second catheter 150 positioned within the venous vessel wall 114. As shown in FIG. 4A, the distal end 154 of the second catheter 150 may further comprise an expandable balloon 158 coupled with the external surface of the second catheter 150. In operation, the expandable balloon 158 can be used to anchor the distal end 154 of the second catheter 150 in the desired location within the venous vessel wall 114. The expandable balloon 158 may be any expandable balloon that is appropriate for insertion within a vessel and can be formed of any material suitable for this function, including without limitation, polyethylene, latex, polyestherurethane, polyurethane, sylastic, silicone rubber, or combinations thereof.

The expandable balloon 158 is capable of being controlled by a clinician such that it can inflate and/or deflate to the proper size. The sizing of the expandable balloon 158 will differ between patients and applications and it is often important to determine the proper sizing of the expandable balloon 158 to ensure the distal end 154 of the second catheter 150 is securely anchored within the desired location of the vessel wall 114. The accurate size of the expandable balloon 158 can be determined through any technique known in the art, including without limitation, by measuring the compliance of the expandable balloon 158 ex vivo or in vivo. In addition, the distal end 154 of the second catheter 150 may further comprise a plurality of electrodes that are capable of accurately measuring the cross-sectional area of the vessel of interest as is known in the art. For example, the plurality of electrodes may comprise a combination of excitation and detection electrodes as described in detail in the currently pending U.S. patent application Ser. No. 11/891,981 entitled System and Method for Measuring Cross-Sectional Areas and Pressure Gradients in Luminal Organs, and filed on Aug. 14, 2007, which is hereby incorporated by reference in its entirety. In at least one embodiment, such electrodes may comprise impedance and conductance electrodes and may be used in connection with ports for the suction of fluid from the vessel and/or the infusion of fluid therein.

The expandable balloon 158 may be in fluid communication with a secondary lumen 160 disposed within the at least one lumen 156 of the second catheter 150. In this example, the secondary lumen 160 is coupled with a balloon port 162 that extends from the proximal end 152 of the second catheter 150 (see FIG. 3). Accordingly, when the autoretroperfusion system 100 is positioned within a patient, the balloon port 162 can be easily accessed by a clinician, subcutaneously, percutaneously or otherwise, and used to inflate or deflate the expandable balloon 158 with no or minimal invasion to the patient.

As shown in FIGS. 4A and 4B, the distal end 154 of the second catheter 150 may further comprise at least one sensor 166 coupled therewith. In at least one embodiment, the at least one sensor 166 is disposed on the distal end 154 of the second catheter 150 distally of the expandable balloon 158; however, it will be understood that the at least one sensor 166 may be disposed in any location on the distal end 154 of the second catheter 150.

The at least one sensor 166 may be used for monitoring purposes and, for example, may be capable of periodically or continuously monitoring the pressure of the blood flow flowing through the at least one lumen 156 of the first catheter 150 or the venous vessel 14 in which the second catheter 150 is inserted. Additionally, one of the at least one sensors 166 may be used to monitor the pH or the concentrations of carbon dioxide, lactate, or cardiac enzymes within the blood. Furthermore, the at least one sensor 166 is capable of wirelessly communicating the information it has gathered to a remote module through the use of telemetry technology, the interne, or other wireless means, such that the information can be easily accessed by a clinician on a real-time basis or otherwise.

Now referring back to FIG. 3, the autoretroperfusion system 100 further comprises a connector 170. The connector 170 comprises any connector or quick connector known in the medical arts that is capable of forming an anastomosis between an artery and a vein such that oxygenated blood from the arterial system can flow into the venous system. For example, the connector 170 may comprise an annular connector that is capable of coupling with the proximal end 20 of the projection cannula 16 of the catheter 10 and with the proximal end 152 of the second catheter 150 such that arterial blood can flow continuously from the at least one lumen 15 of the catheter 10 to the at least one lumen 156 of the second catheter 150. The connector 170 may be formed of any suitable material known in the art including, but not limited to, silicon rubber, poly(tetrafluoroethene), and/or polyurethane.

The connector 170 of the autoretroperfusion system 100 may comprise a pressure/flow regulator unit that is capable of measuring the flow rate of the blood moving therethrough, the pressure of the blood moving therethrough, and/or other data regarding the blood flowing through the anastomosis. The connector 170 may also be capable of transmitting such gathered data to a remote module 180 through a lead placed intravascularly or, in the alternative, through telemetry or another wireless means. The remote module 180 may comprise any device capable of receiving the data collected by the connector 170 and displaying the same. For example, and without limitation, the remote module 180 may comprise any display device known in the art or a computer, a microprocessor, hand-held computing device or other processing means.

Additionally, the connector 170 may further comprise a means for regulating the blood flow through the anastomosis. One of the main challenges of successfully delivering retroperfusion therapies is that the arterial blood pressure must be reduced prior to being introduced into a vein due to the thinner and more fragile anatomy of venous walls. Indeed, subjecting a non-arterialized venous vessel to the high pressures of arterial blood flow typically results in rupture of the venous vessel. Accordingly, with retroperfusion therapies, it is critical to ensure that the pressure of the arterial blood flow is at least initially controlled such that the venous vessel can arterialize prior to being subjected to the unregulated pressure of the arterial blood flow.

In at least one embodiment the connector 170 may comprise an external compression device to facilitate the control of the flow rate of the blood moving through the anastomosis. Alternatively, other means that are known in the art may be employed to regulate the blood flow and pressure of the blood flowing through the anastomosis formed by the connector 170. In at least one embodiment, the means for regulating the blood flow through the anastomosis formed by the connector 170 is capable of regulating the pressure and/or flow velocity of the blood flowing through the anastomosis. For example, the means for regulating blood flow can be adjusted to ensure that about a 50 mg Hg pressure drop occurs in the blood flow between the arterial vessel and the venous vessel.

The connector 170 is capable of not only transmitting data to the remote module 180, but also receiving commands from the remote module 180 and adjusting the means for regulating blood flow pursuant to such commands. Accordingly, when the autoretroperfusion system 100 is positioned within a patient for retroperfusion therapy, a clinician can use the remote module 180 to view the blood flow data collected by the connector 170 and non-invasively adjust the connector 170 to achieve the desired pressure and/or flow through the anastomosis. Such remote control of the connector 170 is particularly useful as a clinician may incrementally decrease the connector's 170 regulation of the blood flow without surgical intervention during the venous arterialization process and/or after the venous vessel arterializes.

Further, where the remote module 180 comprises a computer or other processing means, the remote module 180 is also capable of being programmed to automatically analyze the data received from the connector 170 and, based on the results thereof, suggest how to adjust the means of regulating the blood flow of the connector 170 and/or automatically adjust the means of regulating the blood flow of the connector 170 to achieve the optimal result. For example, and without limitation, when the autoretroperfusion system 100 is implanted into a patient and the anastomosis is first performed, the remote module 180 can automatically adjust the means for regulating the blood flow of the connector 170 based on the initial blood flow data received by the remote module 180. In this manner, the desired pressure drop between the arterial system and the venous system is immediately achieved and the risk of venous rupture is significantly reduced.

Alternatively, where the connector 170 of the autoretroperfusion system 100 does not comprise a means for regulating blood flow, the gradual arterialization of the venous vessel can be achieved through other techniques known in the art. For example, in at least one embodiment, the autoretroperfusion system 100 further comprises a coil designed to at least partially occlude the vein of interest. In this manner, the pressure is allowed to build in front of the portion of the vein at least partially occluded by the coil and the vein gradually arterializes. In this at least one embodiment, the coil may comprise a metallic memory coil (made of nitinol, stainless steel or other acceptable materials that are radioopaque) and is covered with polytetrafluorethylene, polyethylene terephthalate, polyurethane or any other protective covering available in the medical arts.

Additionally, gradual arterialization can be performed by the second catheter 150. In this embodiment of autoretroperfusion system 100, the at least one lumen 156 of the second catheter 150 is designed to provide an optimal stenosis geometry to facilitate the desired pressure drop as the arterial blood flows therethrough and into the venous system. For example, and without limitation, the at least one lumen 156 may further comprise an internal balloon or resorbable stenosis as disclosed in International Patent Application No. PCT/US2006/029223, entitled "Devices and Methods for Controlling Blood Perfusion Pressure Using a Retrograde Cannula," filed Jul. 28, 2006, which is hereby incorporated by reference herein.

In at least one embodiment, the stenosis comprises an internal expandable balloon (not shown) positioned within the lumen 156 of the second catheter 150. In this at least one embodiment, the internal expandable balloon can be used to provide a pressure drop between the arterial and venous systems as is required to achieve the gradual arterialization of the target vein. The internal expandable balloon and the external expandable balloon 158 of the second catheter 150 may be positioned concentrically or, alternatively, the internal expandable balloon and the expandable balloon 158 may be coupled with distinct portions of the second catheter 150.

The internal expandable balloon may comprise any material suitable in the medical arts, including, without limitation, polyethylene, latex, polyestherurethane, polyurethane, sylastic, silicone rubber, or combinations thereof. Further, the internal expandable balloon may be in fluid communication with a tertiary lumen (not shown) disposed within the at least one lumen 156 of the second catheter 150. In this embodiment, the tertiary lumen is also in fluid communication with an internal balloon port that extends from the proximal end 152 of the second catheter 150. Accordingly, the internal balloon port can be easily accessed by a clinician, subcutaneously, percutaneously or otherwise, and the internal balloon port can be used to inflate or deflate the internal expandable balloon with minimal or no discomfort to the patient when the system 100 is in operation. Alternatively, the internal expandable balloon may be in fluid communication with the at least one lumen 156 of the second catheter 150. In this example, the arterial blood flow through the at least one lumen 156 functions to inflate and deflate the internal expandable balloon in conjunction with the systolic and diastolic components of a heart beat.

The internal expandable balloon may be sized to a specific configuration in order to achieve the desired stenosis. In one embodiment, the size of the desired stenosis may be obtained by measuring the pressure at the tip of the distal end 156 of the second catheter 150 with the at least one sensor 166 while the internal expandable balloon is being inflated. Once the desired intermediate pressure is obtained, the internal expandable balloon volume may then be finalized and the vein is thereafter allowed to arterialize at the modified pressure for a defined period of time. At the end of the defined period (typically about 2-3 weeks), the internal expandable balloon may be removed from the at least one lumen 156 of the second catheter 150.

Insertion and/or removal of the internal expandable balloon from the system 100 may be achieved through the internal balloon port and the related tertiary lumen of the second catheter 150. For example, if the internal expandable balloon is no longer necessary to control the pressure on the venous system because the arterialization of the vein is substantially complete, the internal expandable balloon can be deflated through use of internal balloon port and withdrawn from the system 100 through the tertiary lumen and the internal balloon port.

Other embodiments of the system 100 may comprise other suitable means for providing a stenosis within the at least one lumen 156 of the second catheter 150 such that a pressure drop is achieved in blood flowing therethrough. For example, while a stenosis can be imposed by inflation of the internal expandable balloon, it may also be imposed through positioning a resorbable material within the at least one lumen 156 of the second catheter 150. The resorbable stenosis may be comprised of a variety of materials including, for example and without limitation, magnesium alloy and polyols such as mannitol, sorbitol and maltitol. The degradation rate of the resulting resorbable stenosis will be dependent, at least in part, upon on what type of material(s) is selected to make-up the resorbable stenosis and the same may be manipulated to achieve the desired effect.

In addition to the aforementioned components of the autoretroperfusion system 100, the autoretroperfusion system 100 may further include a first graft 185 and a second graft 190 as shown in FIG. 3. In this embodiment, the first graft 185 is coupled with the proximal end 20 of the projection cannula 16 (that extends through the exterior arterial wall 116) and the connector 170. Further, the second graft 190 is coupled with the proximal end 152 of the second catheter 150 (positioned within the venous vessel wall 114) and the connector 170. Accordingly, in this at least one embodiment, the second graft 190 is capable of traversing the venous vessel wall 114 in such a manner that the anastomosis is sealed and no blood flow is allowed to leak from the anastomosed vein 114.

In this manner, the first and second grafts 185, 190 facilitate the formation of an elongated anastomosis between the venous and arterial vessels 114, 116 and thereby relieve any pressure that may be applied to the two vessels 114, 116 due to the anastomosis formed therebetween. For example and without limitation, in at least one embodiment the combined length of the grafts 185, 190 and the connector 170 is about 6 centimeters. However, it will be understood that the grafts 185, 190 may comprise any length(s) so long as the dimensions allow for an anastomosis to form between the applicable vessels and a fully developed blood flow is achieved from the artery to the venous vessel of interest.

Alternatively, the autoretroperfusion system 100 may only comprise the second graft 190 in addition to the catheter 10, the second catheter 150 and the connector 170. In this embodiment, the connector 170 is coupled with the proximal end 20 of the projection cannula 16 and the second graft 190. Furthermore, the second graft 190 is further coupled with the proximal end 152 of the second catheter 150 such that the second graft 190 traverses an opening within the venous vessel wall 114 (see FIG. 5).

The grafts 185, 190 may comprise any biocompatible, non-resorbable material having the necessary strength to support the surrounding tissue and withstand the pressure asserted by the blood flow therethrough. Furthermore, the grafts 185, 190 must exhibit the necessary flexibility to form an anastomosis between the vein and the artery within which the catheter 10 and the second catheter 150 are respectively housed. For example, and without limitation, the grafts 185, 190 may comprise any conventional implant including synthetic and natural prosthesis, grafts, and the like. The grafts 185, 190 may also comprise a variety of suitable materials, including those conventionally used in anastomosis procedures, including, without limitation, natural and synthetic materials such as heterologous tissue, homologous tissue, polymeric materials, Dacron, fluoropolymers, and polyurethanes. For example, and without limitation, the first and second grafts 185, 190 may comprise a material such as GORE-TEX (polytetraflouroethylene). The grafts 185, 190 may be coated with heparin or any other suitable anti-coagulant. Accordingly, the first graft 185 and the second graft 190 may be placed within a vessel or have blood flow therethrough for an extended period of time without inhibiting blood flow due to coagulation.

In at least one embodiment of the autoretroperfusion system 100, the components of the system 100 are available in a package. Here, the package may also contain at least one sterile syringe containing the fluid to be injected into the balloon port 62 to inflate the expandable balloon 58 of the catheter 10 and/or the balloon port 162 to inflate the expandable balloon 158 of the second catheter 150. Furthermore, the package may also contain devices to facilitate delivery of the autoretroperfusion system 100 such as venous and arterial access devices, a delivery catheter, a guidewire and/or mandrel, an introducer to maintain the catheter 10 in the collapsed position during delivery and, in those embodiments where a coil is used to arterialize the vein of interest, a pusher bar as is known in the art.

The guidewire facilitates the delivery of the autoretroperfusion system 100 into a vessel by providing support to the components thereof. The guidewire may comprise any guidewire known in the art. Furthermore, the distal end of the guidewire may comprise a plurality of impedance electrodes that are capable of taking measurements of the size and vessel in which the guidewire is inserted through the use of impedance technology. Additionally, in at least one embodiment, the impedance electrodes may be further capable of communicating such measurements to the remote module 180 through telemetry or other wireless means in a manner similar to the at least one sensor 166 of the distal end 154 of the second catheter 150. In at least one embodiment, the distal end of the guidewire may comprise two tetrapolar sets of impedance electrodes disposed on its distal-most tip.

Based on the information gathered by the impedance electrodes, a clinician can obtain accurate measurements of a selective region of a vessel. In this manner, the expandable balloon 158 coupled with the distal end 154 of the second catheter 150 may be properly sized and the amount of fluid or gas needed to inflate the expandable balloon 158 can be determined prior to introducing the second catheter 150 into the vein of interest. For example, a clinician can use the plurality of impedance electrodes on the guidewire to obtain measurements of the size and shape of the sub-branches of the coronary sinus. Details regarding the specifications and use of the impedance electrodes are described in detail in the currently pending U.S. patent application Ser. No. 10/782,149 entitled "System and Method for Measuring Cross-Sectional Areas and Pressure Gradients in Luminal Organs," and filed on Feb. 19, 2004, which is hereby incorporated by reference herein in its entirety.

Figure 5:
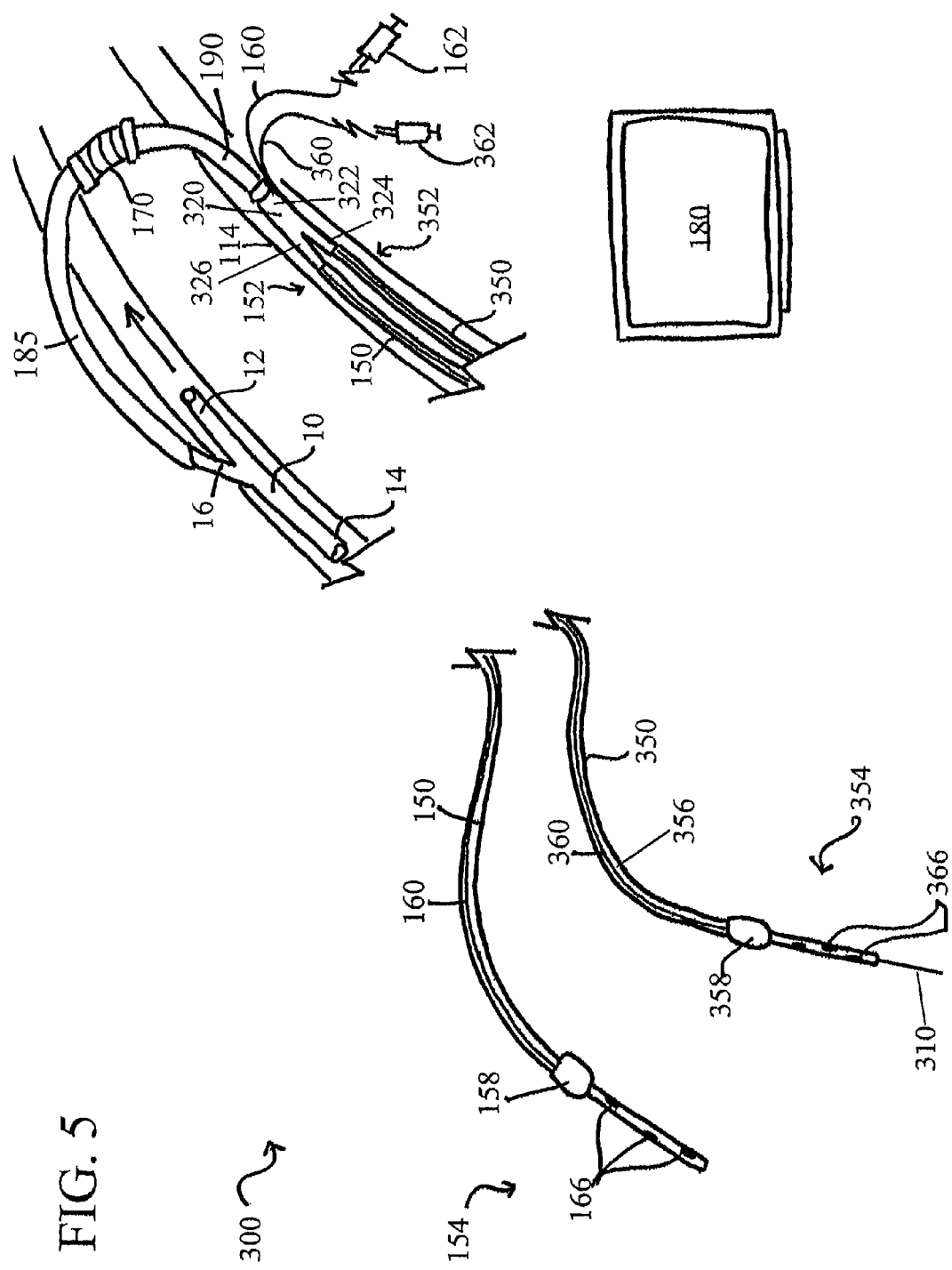
FIG. 5 shows the components of an autoretroperfusion system that can be used to deliver retroperfusion therapy to ischemic tissue.

Now referring to FIG. 5, components of a simultaneous selective autoretroperfusion system 300 are shown. The simultaneous selective autoretroperfusion system 300 (the "SSA system 300") are configured identically to the autoretroperfusion system 100 except that the SSA system 300 further comprises a third catheter 350 and a Y connector 320, both configured for placement within the venous vessel wall 114. Specifically, the SSA system 300 comprises the catheter 10, the second catheter 150, the third catheter 350, the connector 170, and the Y connector 320. It will be understood that the SSA system 300 can also further comprise the first graft 185 and/or the second graft 190, and the remote module 180 as described in connection with autoretroperfusion system 100.

The third catheter 350 is configured for placement within the venous vessel wall 114 adjacent to the second catheter 150. The third catheter 350 is configured identically to the second catheter 150 and comprises a flexible tube having a proximal end 352, a distal end 354 and at least one lumen 356 extending between the proximal end 352 and the distal end 354. Both the proximal end 352 and the distal end 354 of the third catheter 350 are open and in communication with the at least one lumen 356 of the third catheter 350, thereby allowing blood to flow into the at least one lumen 356 through the proximal end 352 and out of the distal end 354 back into the venous vessel 114.

The third catheter 350 may be any catheter known in the art that is capable of intravascular insertion and advancement through the venous system. The third catheter 350 may comprise any appropriate material, including without limitation, polyurethane or silicone rubber. In at least one embodiment, the third catheter 350 is configured to receive a guidewire 310 (see FIGS. 5 and 6) through the at least one lumen 356 in order to facilitate the intravascular delivery of the distal end 354 of the third catheter 350 into the desired location of the venous vessel 114. Furthermore, the third catheter 350 is coated with heparin or any other suitable anti-coagulant prior to insertion in order to facilitate the extended placement of the third catheter 350 within the venous vessel 114.

As shown in FIG. 5, the distal end 354 of the third catheter 350 further comprises an expandable balloon 358 coupled with the external surface of the third catheter 350. In operation, the expandable balloon 358 can be used to anchor the distal end 354 of the third catheter 350 in the desired location within the venous vessel wall 114. The expandable balloon 358 may be any expandable balloon that is appropriate for insertion within a vessel and can be formed of any material suitable for this function, including without limitation, polyethylene, latex, polyestherurethane, polyurethane, sylastic, silicone rubber, or combinations thereof.

Similar to the expandable balloon 158 of the second catheter 150, the expandable balloon 358 is capable of being controlled by a clinician such that it can inflate and/or deflate to the proper size. The appropriate size of the expandable balloon 358 can be determined through any technique known in the art, including without limitation, by measuring the compliance of the expandable balloon 358 ex vivo or in vivo. Furthermore, when the guidewire 310 is used to facilitate the delivery of the distal end 354 of the third catheter 350 into the desired location within the venous vessel wall 114, the electrodes on the distal end of the guidewire 310 may be used to accurately measure the cross-sectional area of the venous vessel 114 such that the expandable balloon 358 can be precisely sized prior to insertion into the vein 114.

In this at least one embodiment, the expandable balloon 358 is in fluid communication with a secondary lumen 360 disposed within the at least one lumen 356 of the third catheter 350. In this example, the secondary lumen 360 is coupled with a balloon port 362 that extends from the proximal end 352 of the third catheter 350. Accordingly, when the SSA system 300 is positioned within a patient, the balloon port 362 can be easily accessed by a clinician, subcutaneously, percutaneously or otherwise, and used to inflate or deflate the expandable balloon 358 with no or minimal invasion to the patient.

Similar to the second catheter 150, the distal end 354 of the third catheter 350 may further comprise at least one sensor 366 coupled therewith. The at least one sensor 366 may be configured identically to the at least one sensor 166 of the second catheter 150 and, accordingly, the at least one sensor 366 may be used to monitor the pressure of blood flow through the at least one lumen 356 of the third catheter 350 or the venous vessel 114 or to monitor the pH or the concentrations of carbon dioxide, lactate, or cardiac enzymes within the blood. Furthermore, the at least one sensor 366 is capable of communicating the data it gathers to the remote module 180 through the use of a wireless technology such that a clinician can easily access the gathered information on a real-time basis or otherwise. In at least one embodiment, the at least one sensor 366 is disposed on the distal end 354 of the third catheter 350 distally of the expandable balloon 358; however, it will be understood that the at least one sensor 366 may be disposed in any location on the distal end 354 of the third catheter 350.

The Y connector 320 of the SSA system 300 comprises flexible material and has a proximal end 322, a distal end 324 and at least one lumen 326 extending between the proximal and distal ends 322, 324. The proximal end 322 of the Y connector 322 is open and configured to be securely coupled with the graft 190. The distal end 324 of the Y connector 322 comprises two open ends which extend from the body of the Y connector 322 in a substantially Y-shaped configuration. The two open ends of the distal end 324 of the Y connector 322 thereby divide the at least one lumen 326 into two separate channels and thus the blood flowing through the at least one lumen 326 is yet again bifurcated.

The proximal end 152 of the second catheter 150 is coupled with one of the two open ends of the distal end 324 of the Y connector 322, thereby receiving a portion of the blood flow that flows through the at least one lumen 326 of the Y-connector. Similarly, the proximal end 352 of the third catheter 350 is coupled with the other open end of the distal end 324 of the Y connector 322 and, thus, the third catheter receives a portion of the blood flow that flows through the at least one lumen 326 of the Y-connector. In this manner, the SSA system 300 can be used to simultaneously retroperfuse more than one ischemic area of the body.

Figure 6:
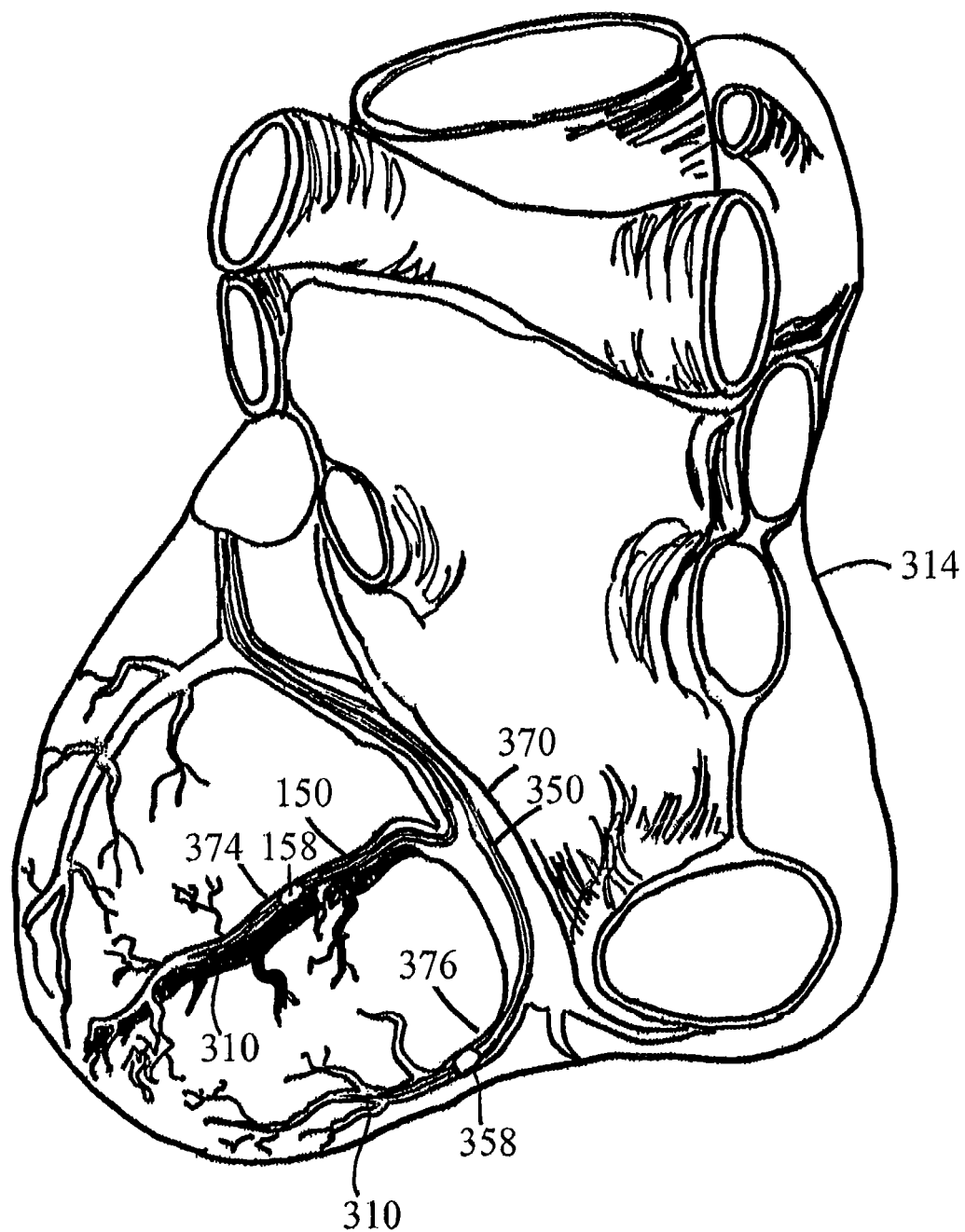
FIG. 6 shows a view of the base and diaphragmatic surface of a heart with the distal ends of two components of the autoretroperfusion system of FIG. 5 positioned therein such that the autoretroperfusion system can deliver simultaneous selective autoretroperfusion therapy thereto.

In application, the second catheter 150 and the third catheter 350 are positioned adjacent to each other within the venous vessel wall 114 as shown in FIG. 5. Furthermore, the distal ends 154, 354 of the second and third catheters 150, 350, respectively, may be placed within different veins such that the arterial blood is delivered to selective portions of ischemic tissue. For example, as shown in FIG. 6, in at least one embodiment the SSA system 300 can be applied to a heart 314 to provide an arterial blood supply to two separate coronary veins, or sub-branches, simultaneously. In this at least one embodiment, the distal ends 154, 354 of the second and third catheters 150, 350 are both advanced through the coronary sinus 370. As the diameter of the coronary sinus 370 ranges from about 10 to about 20 millimeters, cannulating the coronary sinus 370 with both the second and third catheters 150, 350 does not occlude the normal antegrade flow of the blood therethrough. Upon reaching the veins or sub-branches of interest, the distal ends 154, 354 of the second and third catheters 150, 350 are each independently positioned within the veins of interest. In the example shown in FIG. 6, the second catheter 150 is positioned within the interventricular vein 374 and the distal end 354 of the third catheter 350 is positioned within the middle cardiac vein 376. As with autoretroperfusion system 100, the expandable balloons 158, 358 are inflated through balloon ports 162, 362, respectively (shown in FIG. 5), such that the distal ends 154, 354 of the second and third catheters 150, 350 are securely anchored in the desired location within the veins of interest. In this manner, the SSA system 300 can deliver controlled arterial blood flow to, and thus arterialize, two areas of the heart 314 simultaneously.

In at least one embodiment of the SSA system 300, the components of the system 300 are available in a package. Here, the package may also contain sterile syringes with the fluids to be injected into the balloon ports 162, 362 to inflate the expandable balloons 158, 358, respectively. Furthermore, the package may also contain devices to facilitate delivery of the SSA system 300 such as arterial and venous access devices, a delivery catheter, at least two guidewires (configured as described in connection with the delivery of autoretroperfusion system 100), an introducer to maintain the catheter 10 in the collapsed position during delivery and, in those embodiments where a coil is used to arterialize the vein of interest, a pusher bar as is known in the art.

Now referring to FIG. 7, a flow chart of a method 400 for performing automatic retroperfusion using the system 100 is shown. While the method 400 is described herein in connection with treating a heart through catheterization of the coronary sinus, it will be understood that the method 400 may be used to perform autoretroperfusion on any organ or tissue in need of retroperfusion treatment.

Method 400, and the embodiments thereof, can be performed under local anesthesia and do not require any arterial sutures. Further, once implanted, the system 100 can deliver chronic treatment to the patient as the system 100 is capable of remaining within a patient's vascular system for an extended period of time. In this manner, the system 100 and method 400 can be used to treat no-option patients and greatly enhance their quality of life.

Figure 8A:
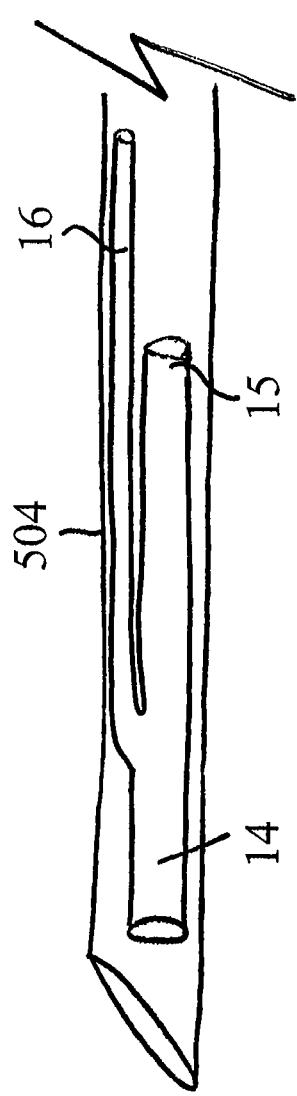
FIG. 8A shows a side view of the catheter of FIG. 1 in a collapsed position within an introducer.
Figure 8B:
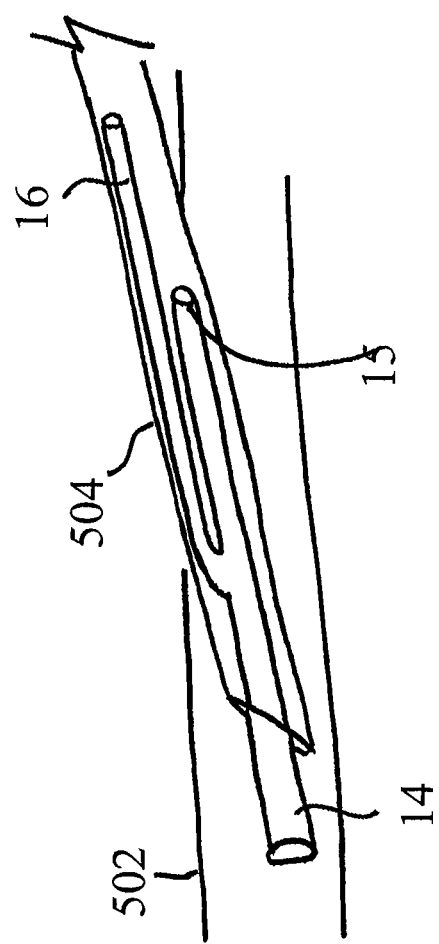
FIG. 8B, shows a side view of the catheter of FIG. 1 being introduced via an introducer into an arterial vessel.

As shown in FIG. 7, in one approach to the method 400, at step 402 an artery 502 of interest is percutaneously punctured under local anesthesia with a conventional artery access device or as otherwise known in the art. For example and without limitation, in at least one embodiment, an 18 gauge needle is inserted into the femoral or subclavian artery. At step 404, the catheter 10 housed in a collapsed position within an introducer 504 (see FIG. 8A) is inserted into the artery 502 of interest. After the distal end 14 of the catheter 10 is positioned in the desired location within the artery 502, the introducer 504 is proximally withdrawn from the artery 502 as shown in FIG. 8B, leaving the catheter 10 positioned therein.

Figure 8C:
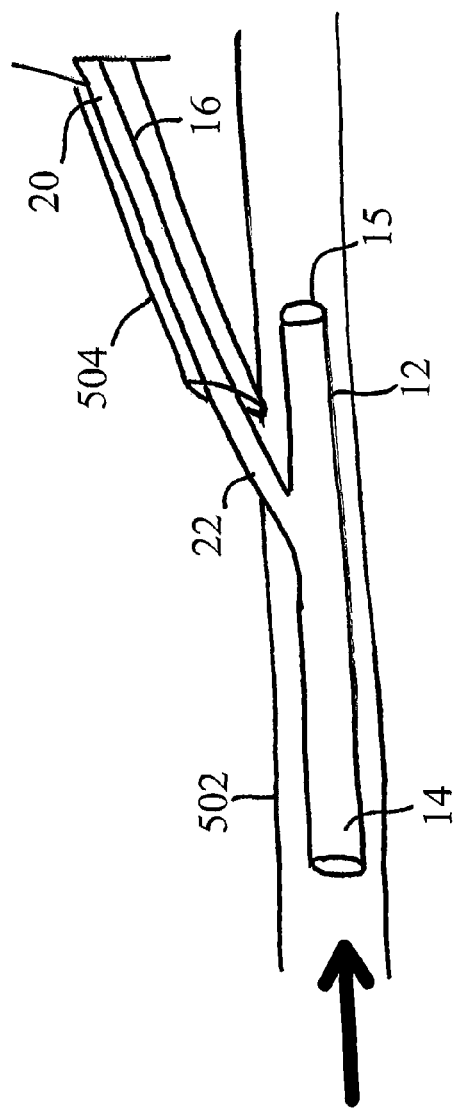
FIGS. 8C and 8D show side views of the introducer of FIG. 8A being removed from an arterial vessel, thereby deploying the projection cannula of the catheter of FIG. 1.
Figure 8D:
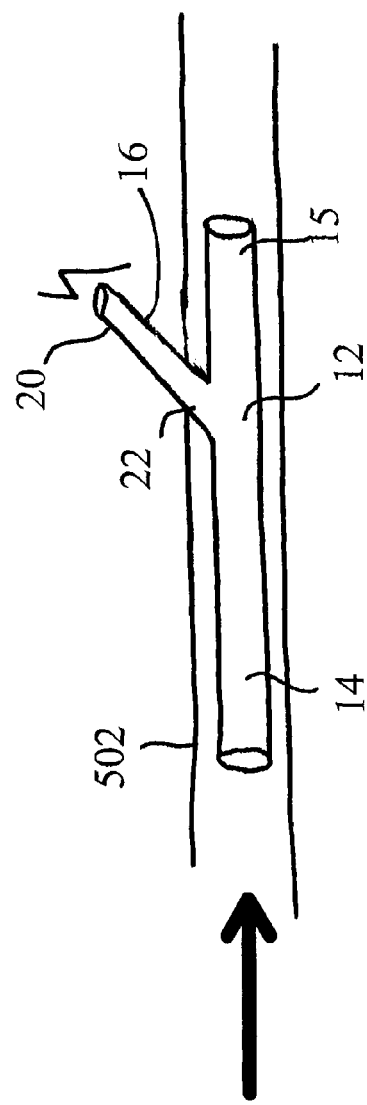

In at least one embodiment, the projection cannula 16 is configured such that when the introducer 504 is withdrawn in a proximal direction, the proximal end 12 of the catheter 10 is released from the introducer 504 before the proximal end 20 of the projection cannula 16 is released from the introducer 504. In this manner, the proximal end 12 of the catheter 10 is delivered within the interior of the arterial wall 502, while the projection cannula 16 remains housed within the interior of the introducer 504 as shown in FIG. 8C. Furthermore, because the introducer 504 no longer applies downward pressure to the projection cannula 16 relative to the proximal end 12 of the catheter 10, the projection cannula 16 is allowed to shift from the collapsed position to the expanded position and therefore extends in a direction that is not parallel with the artery 502 or the body of the catheter 10. In this manner, as shown in FIGS. 8C and 8D, the proximal end 20 of the projection cannula 16 is directed through the opening formed in the arterial wall 502 by the introducer 504.

Accordingly, when the catheter 10 is positioned within the artery 502, the antegrade blood arterial blood flow is allowed to continue through the artery 502 through the proximal end 12 of the catheter 10, while only a portion of the arterial blood is rerouted through the projection cannula 16 and into the veins 506 of interest. In this manner, the normal blood flow through the artery 502 is not inhibited by operation of the autoretroperfusion system 100. Furthermore, in addition to bifurcating the blood flowing through the artery 502, the projection cannula 16 traversing the arterial wall 502 further functions to anchor the catheter 10 in the desired position within the artery 502.

In the embodiment where the catheter 10 further comprises the expandable balloon 58 (see FIG. 1), step 404 may further comprise inflating the expandable balloon 58 to the desired size by injecting fluid into the balloon port 62. In this manner, the expandable balloon 58 functions to further anchor the catheter 10 in the desired location within the artery 502 and seal the opening in the artery 502 through which the projection cannula 16 projects (see FIG. 8E).

At step 406, a vein 506 of interest is percutaneously punctured under local anesthesia with a conventional venous access device or as otherwise known in the art. For example and without limitation, in at least one embodiment, an 18 gauge needle is inserted into the femoral or subclavian vein. At step 408, a delivery catheter 508 is inserted into and advanced through the vein 506 to catheterize the coronary sinus ostium. A guidewire 510 is then inserted at step 410 into the delivery catheter 510 and advanced into the lumen of the vein 506 through the distal end of the delivery catheter 510. Furthermore, the guidewire 510 is advanced into the region of interest by use of x-ray (i.e. fluoroscopy), direct vision, transesophageal echocardiogram, or other suitable means or visualization techniques.

Figure 9:
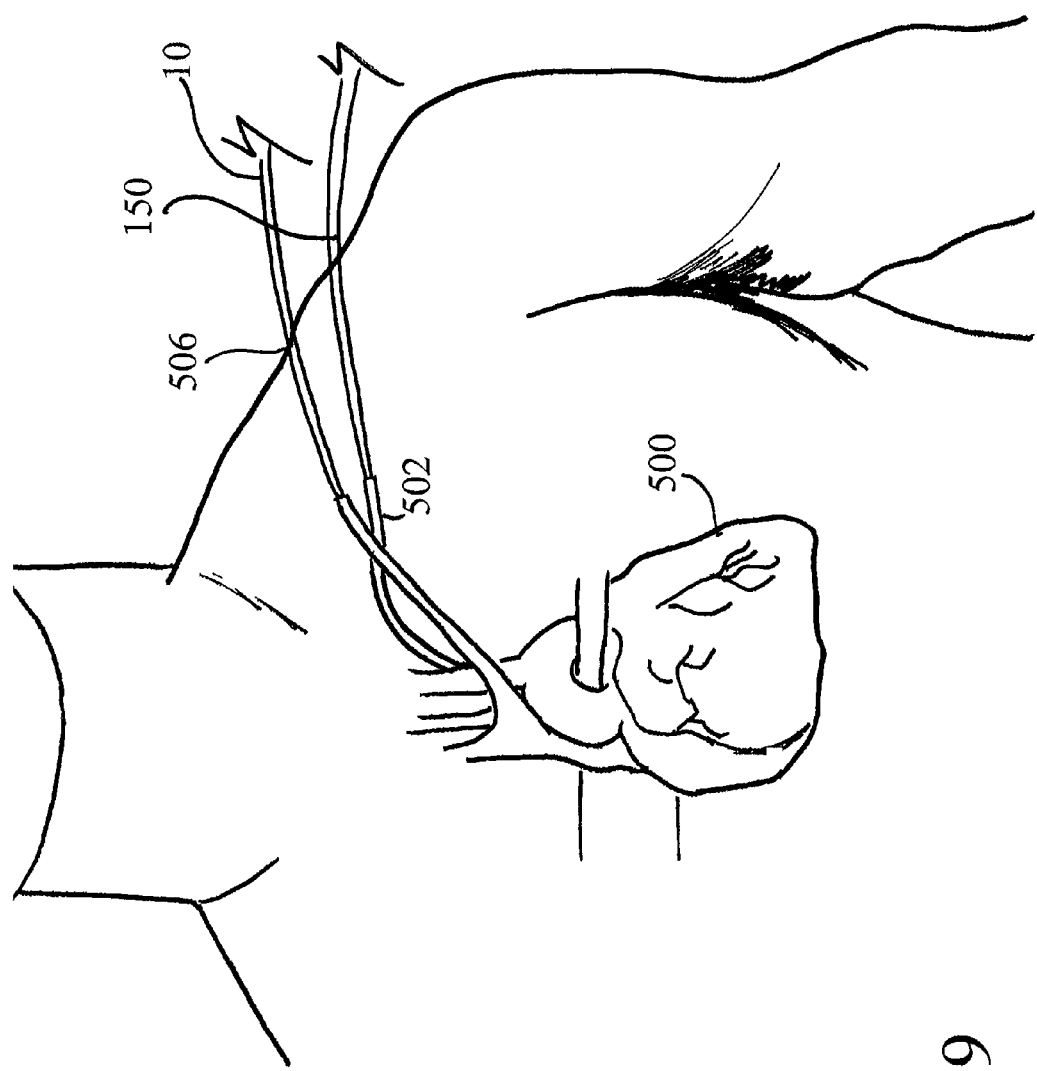
FIG. 9 shows a schematic view of the autoretroperfusion system of FIG. 5 as applied to a heart.
Figure 10:
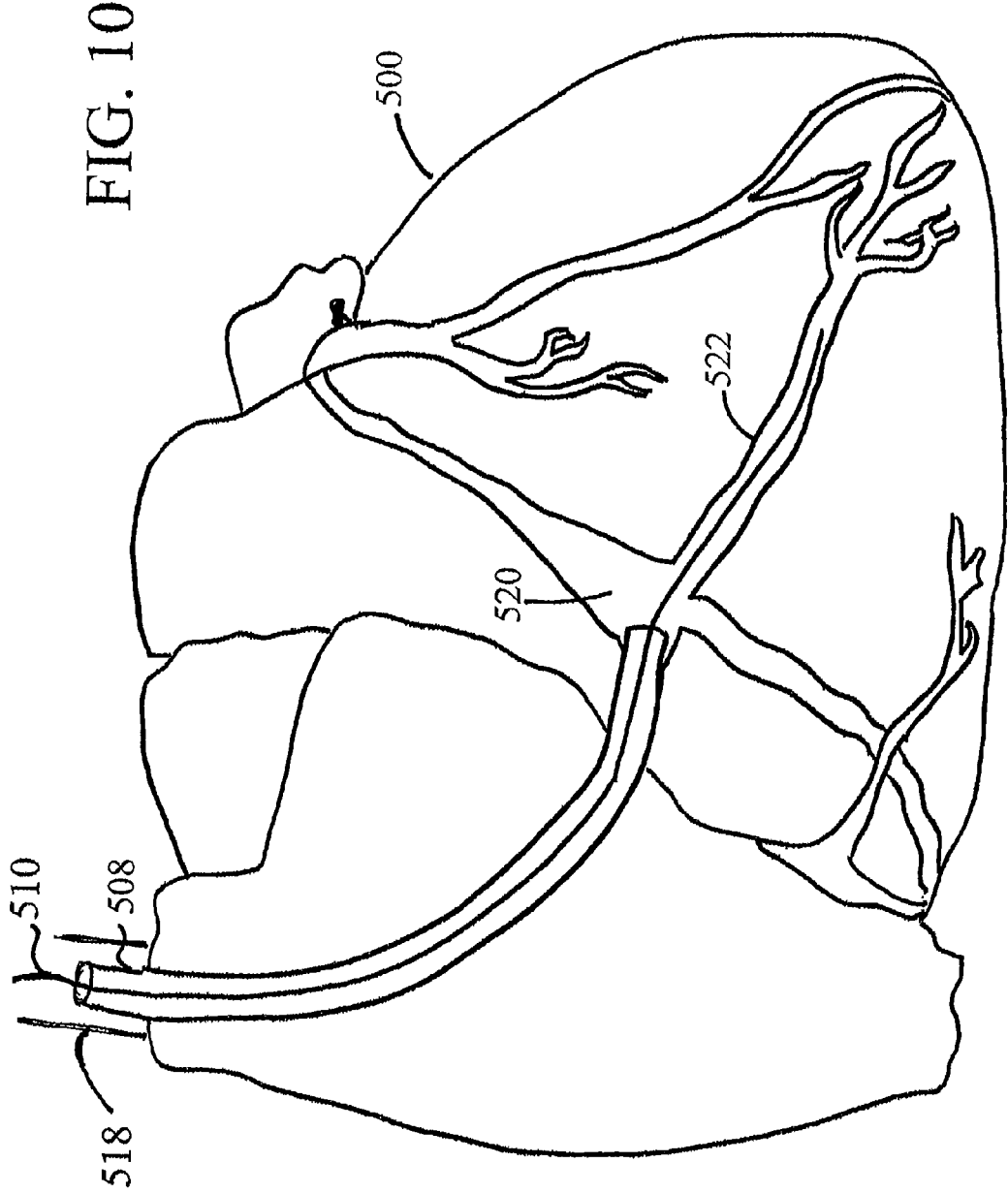
FIG. 10 shows a schematic view of the autoretroperfusion system of FIG. 5 as applied to a heart.

FIGS. 9 and 10 show schematic views of the method 400 as applied to a heart 500. Specifically, in this at least one embodiment, at steps 402 and 404 the artery 502, which in FIG. 9 comprises the subclavian artery, is punctured and the catheter 10 is inserted and positioned therein. Further, at step 406 the vein 506, which in FIG. 9 comprises the subclavian vein, is punctured and at step 408 the delivery catheter 508 is advanced through the superior vena cava 518 and into the coronary ostium of the coronary sinus 520. As shown in FIG. 10, at step 410, the guidewire 510 is advanced through the coronary sinus 520 and into the vein of interest, which, in this at least one embodiment, comprises the posterior vein 522 of the heart 500.

Now referring back to FIG. 7, the guidewire 510 inserted into the vein 506 at step 410 may further comprise a plurality of impedance electrodes as previously described herein. In this approach, the guidewire 510 may be used at optional step 411 to determine the size of the vessel of interest through use of the plurality of impedance electrodes disposed thereon. In this manner, a clinician can use the measurements generated by the impedance electrodes to select a properly sized expandable balloon 158 for use in connection with the second catheter 150. By using a precisely sized expandable balloon 158 and inflation volume, the clinician can ensure that the distal end 154 of the second catheter 150 is securely anchored within the vessel of interest without imposing an undue force on the venous vessel walls.

Figure 11:
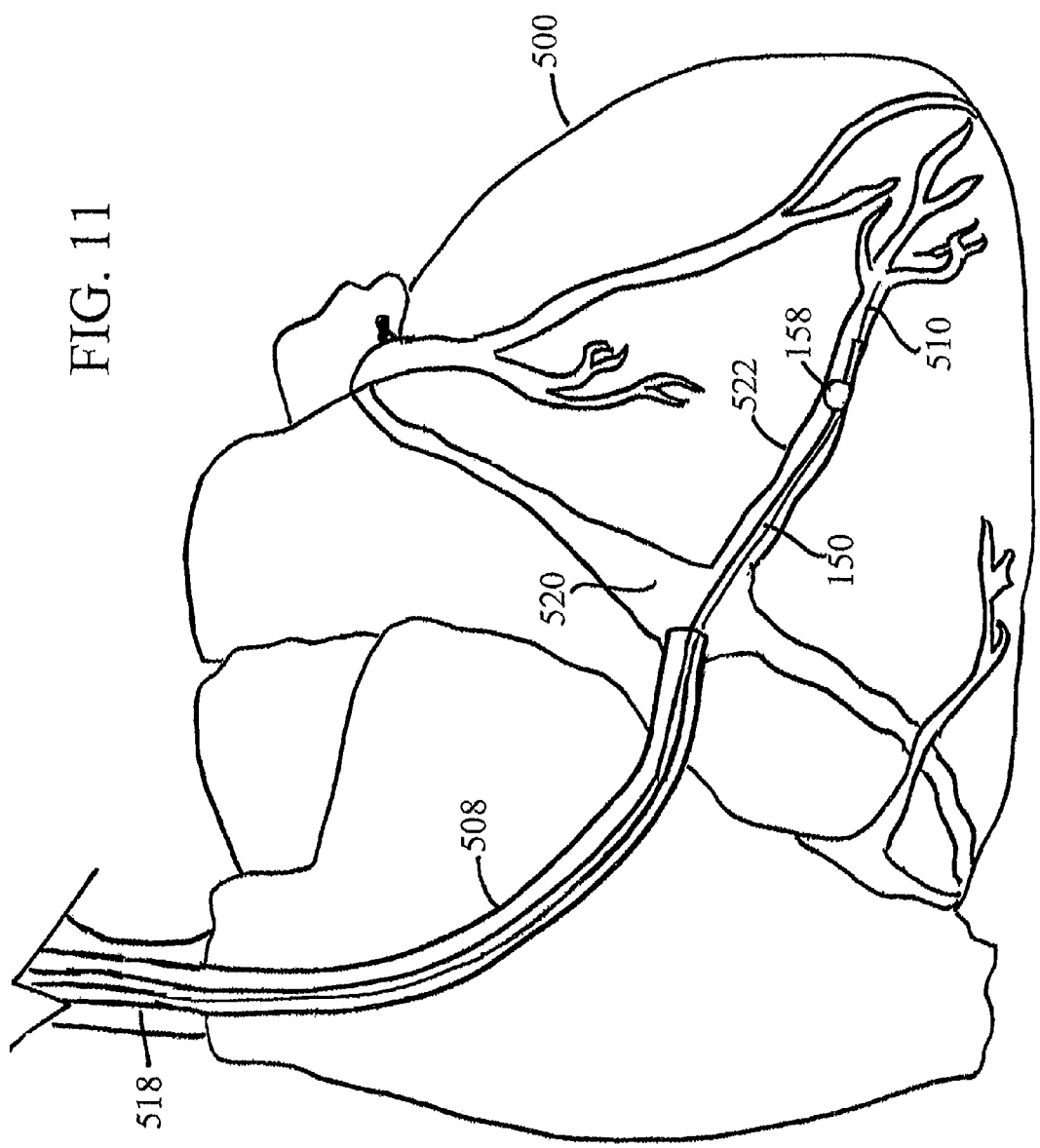
FIG. 11 shows a schematic view of a step of the method of FIG. 7 as the method is applied to a heart.

After the guidewire 510 has been advanced into the vessel of interest at step 410 and, optionally, the dimensions of the vessel of interest have been measured at step 411, the method 400 advances to step 412. At step 412, the distal end 154 of the second catheter 150 is inserted into the delivery catheter 508 over the guidewire 510. Accordingly, the guidewire 510 is slidably received by the at least one lumen 156 of the second catheter 150. The distal end 154 of the second catheter 150 is then advanced over the guidewire 510 to the region of interest and the expandable balloon 158 of the second catheter 150 is inflated to anchor the distal end 154 within the targeted vessel. FIG. 11 shows a schematic view of the method 400, as applied to the heart 500, after step 412 has been completed. It will be understood that at any point after the distal end 154 of the second catheter 150 is positioned and anchored within the desired location in the targeted vessel, the delivery catheter 508 and the guidewire 510 may be withdrawn from the vein of interest.

After the distal end 154 of the second catheter 150 is secured within the targeted vessel, at step 414 the anastomosis between the vein 506 and the artery 502 is formed. Specifically, in at least one approach, the proximal end 20 of the projection cannula 16 of the catheter 10 is coupled with the proximal end 152 of the second catheter 150 by way of the connector 170. In the at least one embodiment of the system 100 comprising the first graft 185 and the second graft 190, the connector 170 may be coupled with the catheter 10 and the second catheter 150 via the first graft 185 and the second graft 190 to form an elongated anastomosis. Alternatively, in yet another approach, the connector 185 may be coupled with the catheter 10 via the proximal end 20 of the projection cannula 16 and the second catheter 150 via only the second graft 190. It will be understood that any combination of the catheter 10, the second catheter 150 and the first and second grafts 185, 190 may be used in connection with the connector 170 to form the desired anastomosis between the vein 506 and the artery 502.

After the anastomosis is formed and the arterial blood is allowed to flow through the anastomosis and thereby through the connector 170, at step 416 the connector 170 measures the flow rate, pressure and any other desired data of the arterial blood flow. The connector 170 transmits the collected data to the remote module 180 either through intravascularly placed leads or wirelessly, through telemetry or other means. In this manner, a clinician may easily view the blood flow data on the remote module 180 and assess the degree of pressure drop that will be required to preserve and gradually arterialize the vein 506.

At step 418, the pressure of the arterial blood flow through the system 100 is modified to transmit the desired pressure to the venous system. In this step 418 the pressure modification can be achieved through a clinician modifying the means of regulating the blood flow of the connector 170 through remote means or, in at least one embodiment of the system 100, inflating the internal expandable balloon of the second catheter 150 using the internal balloon port in order to partially occlude the flow of arterial blood through the at least one lumen 156 of the second catheter 150. Furthermore, in at least one alternative embodiment of the system 100, a clinician may deliver a resorbable stenosis configured to achieve the necessary pressure drop into the at least one lumen 156 of the second catheter 150 through means known in the art.

Alternatively, as previously described in connection with autoretroperfusion system 100, the remote module 180 may further comprise a computer or other processing means capable of being programmed to automatically analyze the data received from the connector 170 and, based on such data, determine the proper degree of adjustment required in the blood pressure flowing through the anastomosis. In this embodiment, at step 418, the remote module 180 automatically adjusts the means of regulating the blood flow of the connector 170 to achieve the optimal pressure drop. In this manner, the desired pressure drop between the arterial system and the venous system is immediately achieved and the risk of venous rupture is significantly reduced.

In step 420 the method 400 allows the arterial blood having a modified pressure to irrigate the vein 506 for a period of time such that the vein 506 properly arterializes. For example, and without limitation, the patient's venous system may be subjected to the reduced arterial pressure for about fourteen days to allow the vein 506 to adapt to the elevated blood pressure flowing therethrough.

After arterialization of the vein 506 is achieved, at step 422 the patient may optionally undergo a coronary venous bypass graft surgery and the components of the autoretroperfusion system 100 may be removed. However, as previously discussed, even with a properly arterialized vein 506, many patients that require retroperfusion therapy may still not be candidates for a coronary vein bypass graft surgery. In the event that the patient is unable to tolerate such a procedure, after the vein 506 has arterialized at step 420, the method 400 can progress directly to step 424. At step 424, the pressure modification of the arterial blood flowing through the second catheter 150 is ceased. Accordingly, pre-arterialized veins 506 are subjected to the full arterial pressure of the blood flowing through the anastomosis and second catheter 150. In at least one embodiment, a clinician can cease the pressure modification by adjusting the controller 170. Alternatively, in the at least one embodiment where the controller 170 can be automatically adjusted by the remote module 180, the remote module 180 can automatically adjust the controller 170 after the veins 506 have pre-arterialized. Further, where the pressure drop is achieved through the use of an internal expandable balloon positioned within the at least one lumen 156 of the second catheter, the clinician may deflate the internal expandable balloon through the internal balloon port and thereafter withdraw the deflated internal expandable balloon through the tertiary lumen of the second catheter and the internal balloon port. In yet another embodiment where a resorbable stenosis is used to achieve the pressure drop in the arterial blood as it flows through the second catheter 150, the resorbable stenosis can be configured to dissolve after the desired period of time, thereby gradually decreasing the influence the resorbable stenosis has on the pressure of the blood flowing through the at least one lumen 156 of the second catheter over a period of time. Accordingly, the autoretroperfusion system 100 can remain chronically implanted within the patient to deliver oxygen-rich blood to a targeted area of tissue over an extended period of time.

Figure 12:
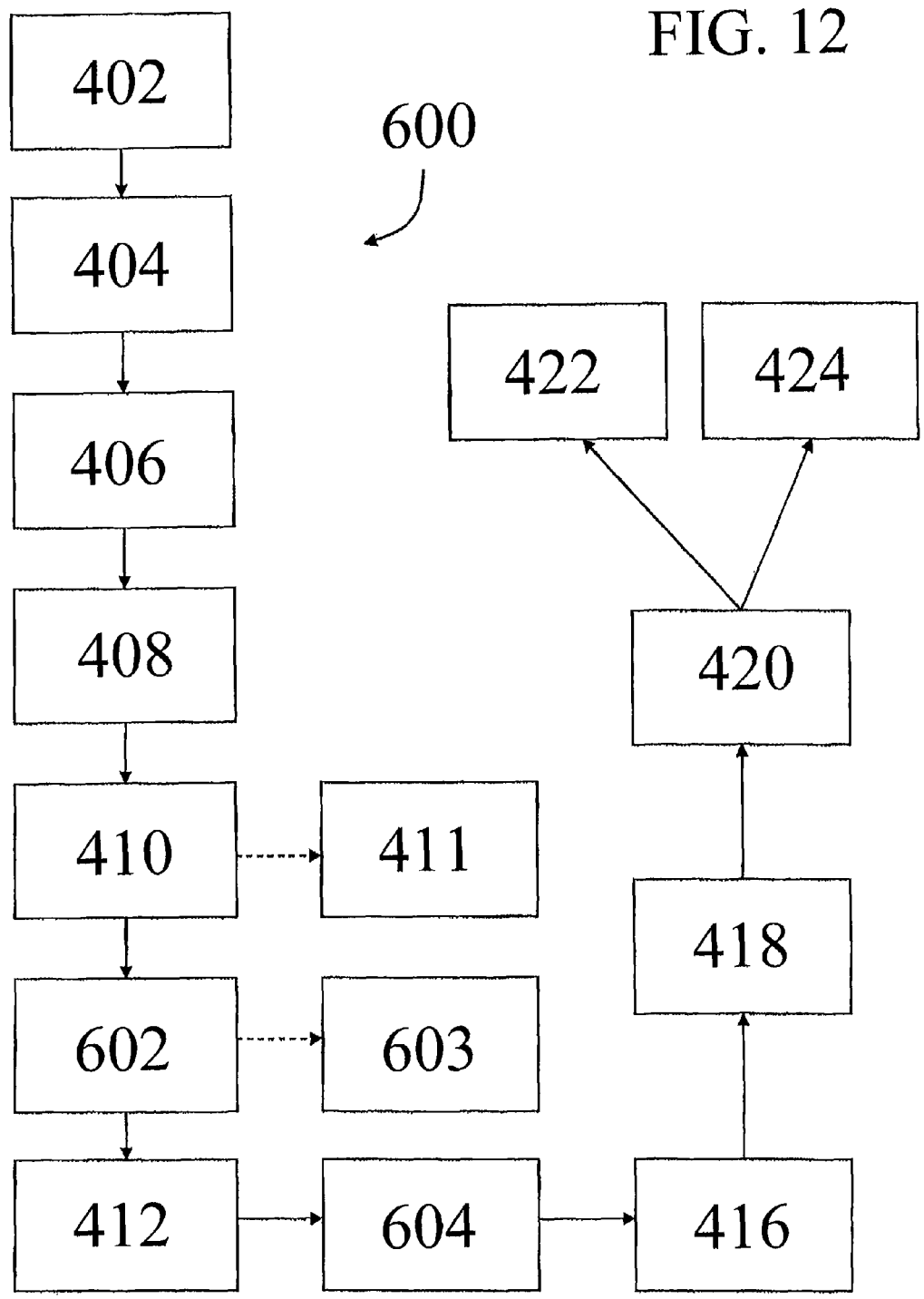
FIG. 12 shows a flow chart of a method for delivering simultaneously selective autoretroperfusion therapy.

Now referring to FIG. 12, a flow chart of a method 600 for performing simultaneous selective retroperfusion using the SSA system 300 is shown. While the method 600 is described herein in connection with treating a heart 500 through catheterization of the coronary sinus 520, it will be understood that the method 600 may be used to perform autoretroperfusion on any organ or tissue in need of retroperfusion treatment. The reference numerals used to identify the steps of method 600 that are included in the description of method 400 designate like steps between the two methods 400, 600. As such, like steps between the two methods 400, 600 will not be discussed in detail with respect to the method 600 and it will be understood that such description can be obtained through the description of the method 400.

Method 600, and the embodiments thereof, can be performed under local anesthesia and does not require arterial sutures. Further, once implanted, the SSA system 300 can deliver simultaneous chronic treatment to multiple ischemic locations as the system 300 is capable of remaining within a patient's vascular system for an extended period of time and selectively retroperfusion more than one sub-branch of a vein 506.

The method 600 progresses through steps 402 through 410 as previously described in connection with the method 400. After the guidewire 510 is advanced through the coronary sinus 520 and into the first vein of interest, a second guidewire 610 is inserted at step 602 into the delivery catheter 508 adjacent to the guidewire 510, and advanced into the lumen of the vein 506 through the distal end of the delivery catheter 510. The second guidewire 610 is then advanced into a second region of interest by use of x-ray (i.e. fluoroscopy), direct vision, transesophageal echocardiogram, or other suitable means or visualization techniques. The second guidewire 610 is configured similar to the guidewire 510 and is capable of functioning the in the same manner.

Figure 13:
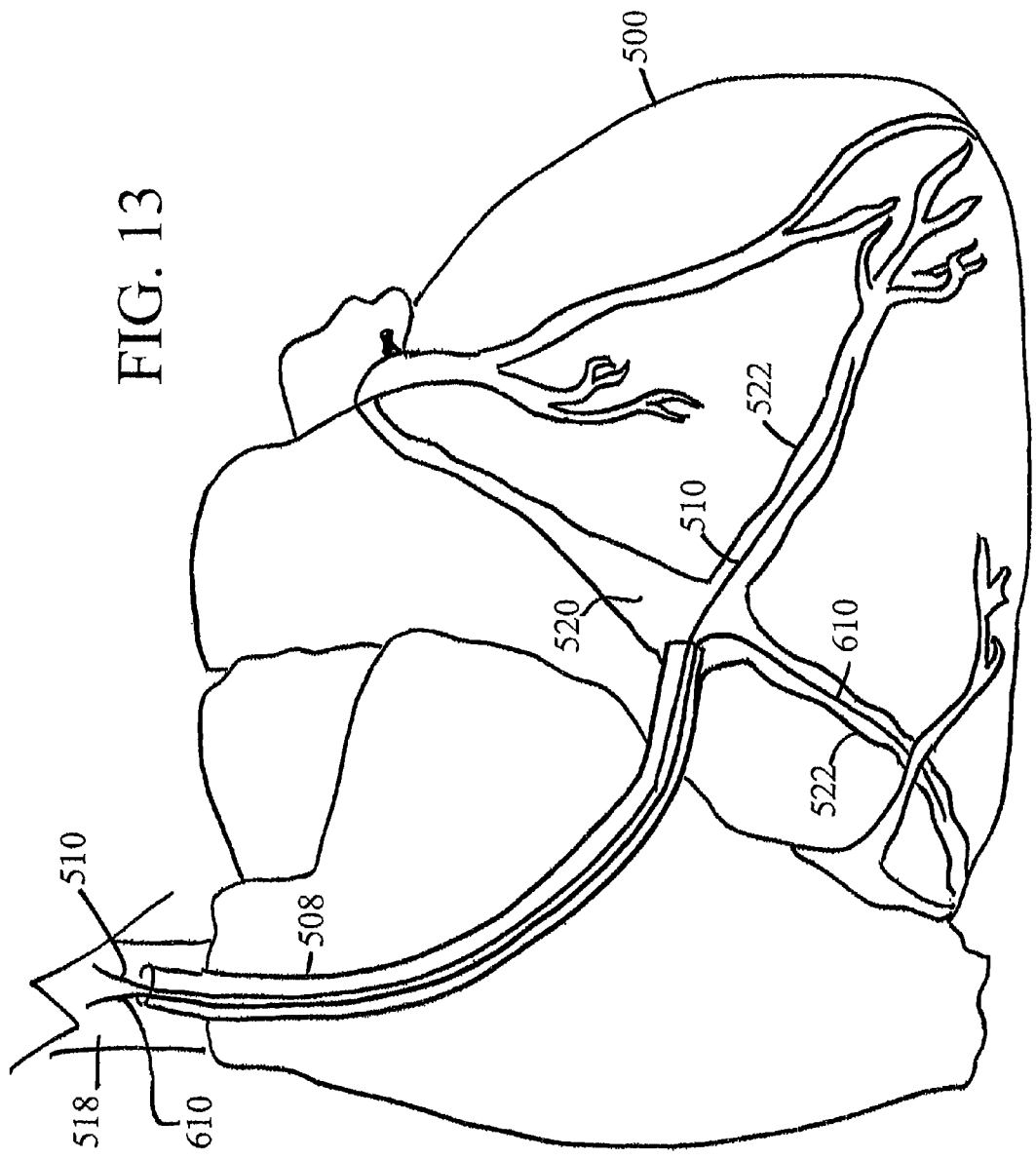
FIG. 13 shows a schematic view of a step of the method of FIG. 12 as the method is applied to a heart.

FIG. 13 shows a schematic view of the method 600 as applied to a heart 500. Specifically, in this at least one embodiment, FIG. 13 shows the method 600 at step 602 wherein the guidewire 510 is inserted a first vein of interest, which comprises the posterior vein 522 of the heart 500, and the second guidewire 610 is inserted into a second vein of interest, which comprises the interventricular vein 622 of the heart 500.

Now referring back to FIG. 12, the guidewire 610 inserted into the second vein of interest in step 602 may further comprise a plurality of impedance electrodes as previously described with respect to the guidewire 510. In this embodiment, the guidewire 610 may be used at optional step 603 to determine the size of the second vessel of interest through use of the plurality of impedance electrodes disposed thereon. In this manner, a clinician can use the measurements generated by the impedance electrodes to select a properly sized expandable balloon 358 for use in connection with the third catheter 350. By using a precisely sized expandable balloon 358 and inflation volume, a clinician can ensure that the distal end 354 of the third catheter 350 is securely anchored within the second vessel of interest without imposing an undue force on the venous vessel walls.

Figure 14:
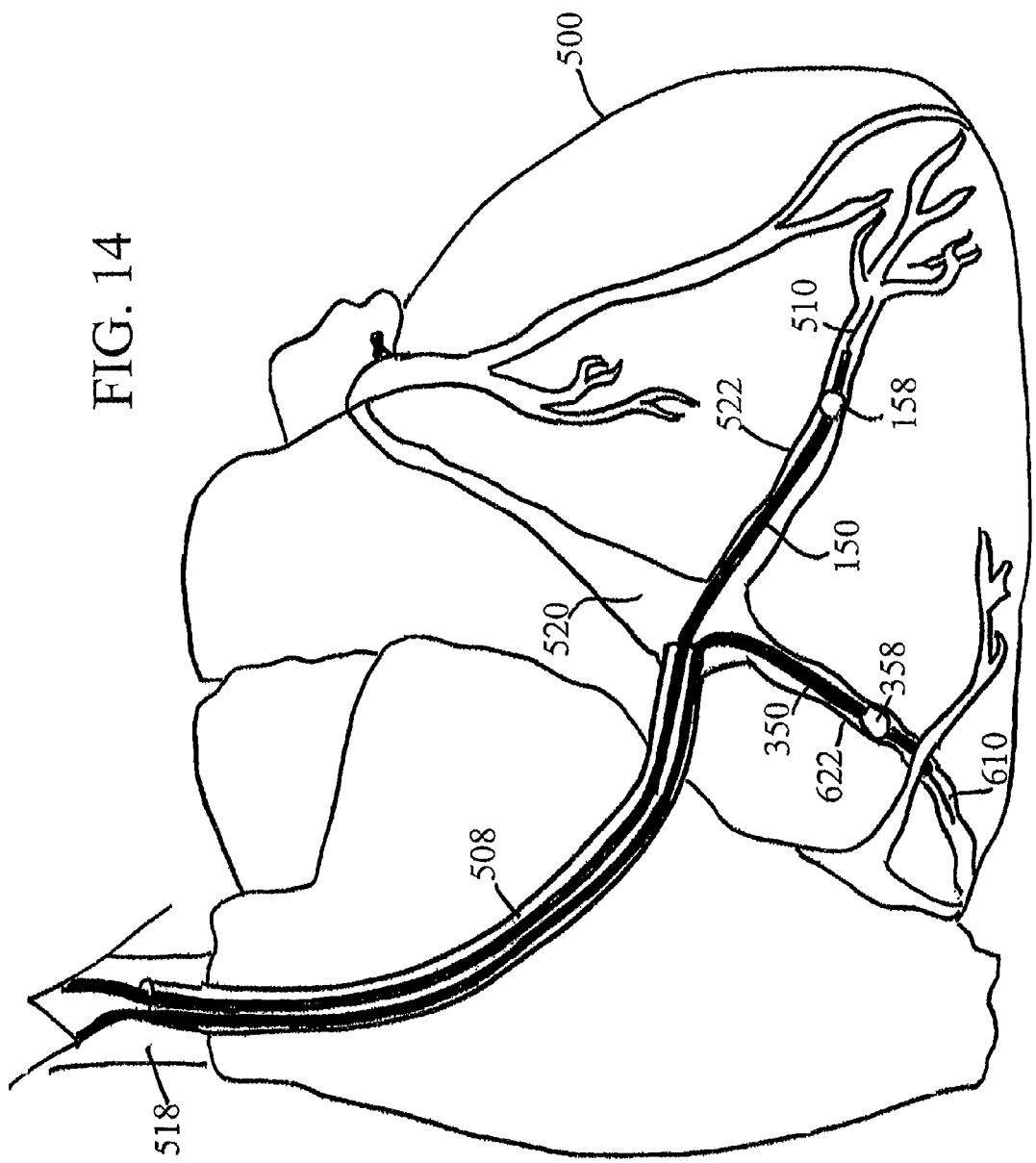
FIG. 14 shows a schematic view of a step of the method of FIG. 12 as the method is applied to a heart.

After the guidewire 610 has been advanced into the second vessel of interest at step 602 and, optionally, the dimensions of the second vessel of interest have been measured at step 603, the method 600 advances to step 412 wherein the second catheter 150 is inserted over the guidewire 510 as described in connection with method 400. At step 604, the distal end 354 of the third catheter 350 is inserted into the delivery catheter 508 over the second guidewire 610. Accordingly, the second guidewire 610 is slidably received by the at least one lumen 356 of the third catheter 350. The distal end 354 of the third catheter 350 is then advanced over the second guidewire 610 to the second region of interest and the expandable balloon 358 of the third catheter 350 is inflated to anchor the distal end 354 within the targeted vessel. FIG. 14 shows a schematic view of the method 600 at step 604 as applied to the heart 500. It will be understood that at any point after the distal ends 154, 354 of the second and third catheters 150, 350 are positioned and anchored in the desired locations within the targeted vessels, the delivery catheter 508 and the guidewires 510, 610 may be withdrawn from the vein 506.

After both the distal end 154 of the second catheter 150 and the distal end 354 of the third catheter 350 are secured within the targeted vessels, the method 600 proceeds to step 414 where the anastomosis is formed between the vein 506 and the artery 502 as described in connection with method 400. Thereafter, the method 600 advances through steps 416 through 424 as described in connection with the method 400. Furthermore, at step 418, it will be recognized that a clinician can independently adjust the pressure drop through the second and third catheters 150, 350 in the event that an internal expandable balloon is used in either or both catheters 150, 350 or resorbable stenosis are employed within the at least one lumens 156, 356 of the second and third catheters 150, 350. Alternatively, in the at least one embodiment where the controller 170 comprises a means for regulating the blood flow through the anastomosis, the pressure of the arterial blood flowing through both the second and third catheters 150, 350 may be substantially the same.

As described herein, the method 600 may be used to simultaneously and immediately treat two different ischemic areas of a tissue through the use of one minimally to non-invasive procedure. Furthermore, the method 600 can provide no-option patients with a viable treatment option that is not associated with contraindications for congestive heart failure, diabetes, or drug treatment.

While various embodiments of devices, systems, and methods for achieving autoretroperfusion of the heart tissue have been described in considerable detail herein, the embodiments are merely offered by way of non-limiting examples of the disclosure described herein. Many variations and modifications of the embodiments described herein will be apparent to one of ordinary skill in the art in light of this disclosure. It will therefore be understood by those skilled in the art that various changes and modifications may be made, and equivalents may be substituted for elements thereof, without departing from the scope of the disclosure. Indeed, this disclosure is not intended to be exhaustive or to limit the scope of the disclosure. The scope of the disclosure is to be defined by the appended claims, and by their equivalents.

Further, in describing representative embodiments, the disclosure may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps disclosed herein should not be construed as limitations on the claims. In addition, the claims directed to a method and/or process should not be limited to the performance of their steps in the order written, and one skilled in the art can readily appreciate that the sequences may be varied and still remain within the spirit and scope of the present disclosure.

It is therefore intended that the disclosure will include, and this description and the appended claims will encompass, all modifications and changes apparent to those of ordinary skill in the art based on this disclosure.

I claim:

1. A catheter for controlling blood perfusion pressure, the catheter comprising:
    an elongated body configured for complete placement within a section of a supply artery, the elongated body having a proximal open end, a distal open end, and at least one lumen extending between the proximal open end and the distal open end; and
    a cannula configured to extend through an opening in the section of the supply artery, the cannula comprising a hollow interior in fluid communication with at least one of the at least one lumens of the elongated body;
    the catheter configured so that when in use and when the proximal open end and the distal open end are each positioned within the section of the supply artery, a first quantity of blood flowing through the supply artery flows through the supply artery, into the distal end of the elongated body, through the at least one lumen, and out of the proximal end of the elongated body back into the supply artery, and a second quantity of blood flows through the hollow interior of the cannula and out of a proximal end of the cannula and ultimately into a vein directly or indirectly connected to the cannula without requiring an external pump to pump blood through the catheter; and
    wherein the catheter is configured to move, relative to the elongated body, between a substantially extended configuration and a substantially collapsed configuration.

2. The catheter of claim 1, wherein the hollow interior of the cannula comprises a first diameter, the at least one lumen comprises a second diameter throughout the elongated body and the first diameter is less than the second diameter.

3. The catheter of claim 2, wherein the cannula extends from the elongated body such that an angle is formed between the cannula and the elongated body, wherein the cannula is movable between a substantially extended configuration wherein the angle comprises between about 15° and about 45° and a substantially collapsed configuration wherein the angle comprises less than about 15°, and wherein the first diameter is sized relative to the second diameter so to achieve a necessary pressure drop of the second quantity of blood when the proximal end of the cannula is in communication with an unarterialized vein.

4. The catheter of claim 1, wherein the cannula extends from the elongated body such that an angle is formed between the cannula and the elongated body, and wherein the cannula is movable between a substantially extended configuration wherein the angle comprises between about 15° and about 90° and a substantially collapsed configuration wherein the angle comprises less than about 15°.

5. The catheter of claim 1, further comprising:
    an expandable balloon coupled with the elongated body; and
    a balloon port in fluid communication with the expandable balloon through a secondary lumen of the catheter, wherein the balloon port is configured for subcutaneous implantation.

6. The catheter of claim 1, wherein the hollow interior of the cannula comprises a diameter having a value between about 2.7 millimeters to about 4 millimeters.

7. The catheter of claim 1, configured in use so that when a second catheter is placed within the vein and connected to the cannula, the second quantity of blood flows through the cannula, into the second catheter, and into the vein, so to achieve arterialization of at least part of the vein over time.

8. The catheter of claim 1, configured in use so that when a second catheter is placed within the vein and when a connector configured to measure data associated with blood flow is connected to the cannula and the second catheter, the second quantity of blood flows through the cannula, into the second catheter via the connector, and into the vein, resulting in retroperfusion that can be regulated based upon the measured data.

9. The catheter of claim 1, wherein the catheter is part of a system for controlling blood perfusion pressure within a vein, the system further comprising:
 a second catheter configured for placement within a venous vessel, the second catheter having a proximal end, a distal end, and at least one lumen extending between the proximal end and the distal end; and
 a connector coupled with the cannula of the first catheter and the proximal end of the second catheter, the connector configured to measure data associated with fluid flowing therethrough and to automatically regulate blood flow based on the measured data.

10. The catheter of claim 9, wherein the cannula is movable, relative to the elongated body, between a substantially extended configuration and a substantially collapsed configuration, and wherein the cannula extends from the elongated body such that an angle is formed between the cannula and the elongated body, the angle comprising between about 15° and about 90° in the substantially extended configuration and comprising less than about 15° in the substantially collapsed configuration, and the cannula being biased towards the substantially extended configuration.

11. The catheter of claim 9, wherein the system further comprises:
 an expandable balloon coupled with either the elongated body of the first catheter or the second catheter; and
 a balloon port in fluid communication with the expandable balloon through a secondary lumen of the elongated body or the second catheter.

12. The catheter of claim 11, wherein the expandable balloon is configured to prevent fluid leakage through the arterial opening when the expandable balloon is in a substantially inflated configuration and the elongated body is positioned within the artery such that the cannula extends through the opening in the artery.

13. The catheter of claim 9, wherein the second catheter comprises an expandable balloon coupled with the exterior of the second catheter, and wherein the second catheter comprises at least one primary lumen and at least one secondary lumen, the expandable balloon in fluid communication with the at least one secondary lumen of the second catheter.

14. The catheter of claim 9, wherein the system further comprises:
 a first graft coupled with the proximal end of the second catheter and the connector such that the at least one lumen of the second catheter is in fluid communication with the at least one lumen of the first catheter; and
 a second graft coupled with the cannula and the connector such that the at least one lumen of the second catheter is in fluid communication with the at least one lumen of the elongated body.

15. The catheter of claim 9, wherein the system further comprises a remote module for receiving the data measured by the connector.

16. The catheter of claim 9, wherein the at least one lumen of the second catheter comprises at least one primary lumen and at least one secondary lumen, and the system further comprises a stenosis positioned within the at least one primary lumen of the second catheter.

17. The catheter of claim 16, wherein the stenosis comprises a first expandable balloon, and wherein the second catheter further comprises a tertiary lumen in fluid communication with the first expandable balloon.

18. The catheter of claim 9, wherein the system further comprises at least one guidewire configured to be slidably inserted within the at least one lumen of the second catheter and having a proximal end and a distal end, wherein the distal end of the at least one guidewire further comprises a plurality of electrodes disposed thereon, and wherein the plurality of electrodes comprise a combination of excitation and detection electrodes.

19. The catheter of claim 9, wherein the system further comprises an expandable balloon coupled with the elongated body of the first catheter in a location adjacent to the cannula, wherein the expandable balloon is configured to prevent fluid leakage through the arterial opening when the expandable balloon is in a substantially inflated configuration and the elongated body is positioned within the artery such that the cannula extends through the opening in the artery.

20. The catheter of claim 19, wherein the system further comprises:
 a third catheter for placement within a venous vessel adjacent to the second catheter, the third catheter having a proximal end, a distal end, and at least one lumen extending between the proximal end and the distal end; and
 a Y-connector configured for placement within the venous vessel and having an open proximal end, a distal end having at least two branches, and a lumen extending between the open proximal end and each of the at least two branches of the distal end;
 wherein the open proximal end of the Y-connector is in fluid communication with the connector, one of the at least two branches of the distal end is in fluid communication with the proximal end of the second catheter, and one of the at least two branches of the distal end is in fluid communication with the proximal end of the third catheter.

21. The catheter of claim 9, wherein the system further comprises:
 a third catheter for placement within a venous vessel adjacent to the second catheter, the third catheter having a proximal end, a distal end, and at least one lumen extending between the proximal end and the distal end; and
 a Y-connector configured for placement within the venous vessel and having an open proximal end, a distal end having at least two branches, and a lumen extending between the open proximal end and each of the at least two branches of the distal end;
 wherein the open proximal end of the Y-connector is in fluid communication with the connector, one of the at least two branches of the distal end is in fluid communication with the proximal end of the second catheter, and one of the at least two branches of the distal end is in fluid communication with the proximal end of the third catheter.

* * * * *